US012575961B2

(12) United States Patent
Glithero

(10) Patent No.: US 12,575,961 B2
(45) Date of Patent: Mar. 17, 2026

(54) FLUID COLLECTION DEVICES, SYSTEMS, AND METHODS

(71) Applicant: PUREWICK CORPORATION, El Cajon, CA (US)

(72) Inventor: Jason Iain Glithero, McDonough, GA (US)

(73) Assignee: PUREWICK CORPORATION, Covington, GA (US)

( * ) Notice: Subject to any disclaimer, the term of this patent is extended or adjusted under 35 U.S.C. 154(b) by 548 days.

(21) Appl. No.: 17/051,399

(22) PCT Filed: Apr. 29, 2019

(86) PCT No.: PCT/US2019/029608
§ 371 (c)(1),
(2) Date: Oct. 28, 2020

(87) PCT Pub. No.: WO2019/212949
PCT Pub. Date: Nov. 7, 2019

(65) Prior Publication Data
US 2021/0228400 A1 Jul. 29, 2021

Related U.S. Application Data

(60) Provisional application No. 62/665,302, filed on May 1, 2018.

(51) Int. Cl.
*A61F 5/453* (2006.01)
*A61F 5/44* (2006.01)
(Continued)

(52) U.S. Cl.
CPC ............ *A61F 5/453* (2013.01); *A61F 5/4401* (2013.01); *A61F 5/4408* (2013.01); *A61F 5/455* (2013.01);
(Continued)

(58) Field of Classification Search
CPC ........ A61F 5/455; A61F 5/453; A61F 13/471; A61F 5/4556; A61F 2013/15146;
(Continued)

(56) References Cited

U.S. PATENT DOCUMENTS

| 670,602 A | 3/1901 | Baker |
| 1,032,841 A | 7/1912 | Koenig |

(Continued)

FOREIGN PATENT DOCUMENTS

| AU | 2018216821 A1 | 8/2019 |
| CA | 2165286 C | 9/1999 |

(Continued)

OTHER PUBLICATIONS

US 9,908,683 B2, 03/2018, Sandhausen et al. (withdrawn)
(Continued)

*Primary Examiner* — Nicholas J. Weiss
*Assistant Examiner* — Seth Han
(74) *Attorney, Agent, or Firm* — Ballard Spahr LLP

(57) ABSTRACT
Examples relate to systems, devices, and methods for removing fluid from a fluid collection device using a portable vacuum source operably coupled thereto. The fluid collection devices include urine collection devices shaped to complement the female or male anatomy near the respective urethras and the vacuum source is operably coupled to the fluid collection device via one or more sections of conduit.

19 Claims, 8 Drawing Sheets

US 12,575,961 B2

Page 2

(51) Int. Cl.
    *A61F 5/455*     (2006.01)
    *A61M 1/00*     (2006.01)

(52) U.S. Cl.
    CPC ....... *A61M 1/80* (2021.05); *A61M 2202/0496*
    (2013.01); *A61M 2210/1092* (2013.01); *A61M*
    *2210/1096* (2013.01)

(58) Field of Classification Search
    CPC .......... A61F 5/451; A61F 5/4553; A61F 5/44;
    A61G 9/006; A61M 25/0017; A61M
    1/60; A61M 2202/0496; A61B 10/007
    See application file for complete search history.

(56)           References Cited

U.S. PATENT DOCUMENTS

| | | | |
|---|---|---|---|
| 1,178,644 | A | 4/1916 | Johnson |
| 1,742,080 | A | 12/1929 | Jones |
| 1,979,899 | A | 11/1934 | Obrien et al. |
| 2,262,772 | A | 11/1941 | Peder |
| 2,326,881 | A | 8/1943 | Packer |
| 2,379,346 | A | 6/1945 | Farrell |
| 2,613,670 | A | 10/1952 | Edward |
| 2,616,426 | A | 11/1952 | Adele |
| 2,644,234 | A | 7/1953 | Earl |
| 2,859,786 | A | 11/1958 | Tupper |
| 2,944,551 | A | 7/1960 | Car |
| 2,968,046 | A | 1/1961 | Duke |
| 2,971,512 | A | 2/1961 | Reinhardt |
| 3,032,038 | A | 5/1962 | Swinn |
| 3,077,883 | A | 2/1963 | Hill |
| 3,087,938 | A | 4/1963 | Hans et al. |
| 3,169,528 | A | 2/1965 | Knox et al. |
| 3,194,238 | A | 7/1965 | Breece |
| 3,198,994 | A | 8/1965 | Hildebrandt et al. |
| 3,221,742 | A | 12/1965 | Egon |
| 3,312,221 | A | 4/1967 | Overment |
| 3,312,981 | A | 4/1967 | Mcguire et al. |
| 3,349,768 | A | 10/1967 | Keane |
| 3,362,590 | A | 1/1968 | Gene |
| 3,366,116 | A | 1/1968 | Huck |
| 3,398,848 | A | 8/1968 | Donovan |
| 3,400,717 | A | 9/1968 | Cubitt et al. |
| 3,406,688 | A | 10/1968 | Cubitt |
| 3,424,163 | A | 1/1969 | Gravdahl |
| 3,425,471 | A | 2/1969 | Yates |
| 3,511,241 | A | 5/1970 | Lee |
| 3,512,185 | A | 5/1970 | Ellis |
| 3,520,300 | A | 7/1970 | Flower |
| 3,528,423 | A | 9/1970 | Lee |
| 3,613,123 | A | 10/1971 | Langstrom |
| 3,648,700 | A | 3/1972 | Warner |
| 3,651,810 | A | 3/1972 | Ormerod |
| 3,661,155 | A | 5/1972 | Lindan |
| 3,699,815 | A | 10/1972 | Holbrook |
| 3,726,277 | A | 4/1973 | Hirschman |
| 3,742,952 | A | 7/1973 | Magers et al. |
| 3,757,355 | A | 9/1973 | Allen et al. |
| 3,788,324 | A | 1/1974 | Lim |
| 3,843,016 | A | 10/1974 | Bornhorst et al. |
| 3,863,638 | A | 2/1975 | Rogers et al. |
| 3,863,798 | A | 2/1975 | Kurihara et al. |
| 3,864,759 | A | 2/1975 | Horiuchi |
| 3,881,486 | A | 5/1975 | Fenton |
| 3,915,189 | A | 10/1975 | Holbrook et al. |
| 3,998,228 | A | 12/1976 | Poidomani |
| 3,999,550 | A | 12/1976 | Martin |
| 4,015,604 | A | 4/1977 | Csillag |
| 4,020,843 | A | 5/1977 | Kanall |
| 4,022,213 | A | 5/1977 | Stein |
| 4,027,776 | A | 6/1977 | Douglas |
| 4,116,197 | A | 9/1978 | Bermingham |
| 4,180,178 | A | 12/1979 | Turner |
| 4,187,953 | A | 2/1980 | Turner |
| 4,194,508 | A | 3/1980 | Anderson |
| 4,200,102 | A | 4/1980 | Duhamel et al. |
| 4,202,058 | A | 5/1980 | Anderson |
| 4,233,025 | A | 11/1980 | Larson et al. |
| 4,233,978 | A | 11/1980 | Hickey |
| 4,246,901 | A | 1/1981 | Frosch et al. |
| 4,257,418 | A | 3/1981 | Hessner |
| 4,270,539 | A | 6/1981 | Frosch et al. |
| 4,281,655 | A | 8/1981 | Terauchi |
| 4,292,916 | A | 10/1981 | Bradley et al. |
| 4,352,356 | A | 10/1982 | Tong |
| 4,360,933 | A | 11/1982 | Kimura et al. |
| 4,365,363 | A | 12/1982 | Windauer |
| 4,387,726 | A | 6/1983 | Denard |
| 4,425,130 | A | 1/1984 | Desmarais |
| 4,446,986 | A | 5/1984 | Bowen et al. |
| 4,453,938 | A | 6/1984 | Brendling |
| 4,457,314 | A | 7/1984 | Knowles |
| 4,476,879 | A | 10/1984 | Jackson |
| 4,526,688 | A | 7/1985 | Schmidt, Jr. et al. |
| 4,528,703 | A | 7/1985 | Kraus |
| D280,438 | S | 9/1985 | Wendt |
| 4,551,141 | A | 11/1985 | McNeil |
| 4,553,968 | A | 11/1985 | Komis |
| 4,581,026 | A | 4/1986 | Schneider |
| 4,610,675 | A | 9/1986 | Triunfol |
| 4,620,333 | A | 11/1986 | Ritter |
| 4,626,250 | A | 12/1986 | Schneider |
| 4,627,846 | A | 12/1986 | Ternstroem |
| 4,631,061 | A | 12/1986 | Martin |
| 4,650,477 | A | 3/1987 | Johnson |
| 4,656,675 | A | 4/1987 | Fajnsztajn |
| 4,681,570 | A | 7/1987 | Dalton |
| 4,692,160 | A | 9/1987 | Nussbaumer |
| 4,707,864 | A | 11/1987 | Ikematsu et al. |
| 4,713,065 | A | 12/1987 | Koot |
| 4,713,066 | A | 12/1987 | Komis |
| 4,743,236 | A | 5/1988 | Manschot |
| 4,747,166 | A | 5/1988 | Kuntz |
| 4,752,944 | A | 6/1988 | Conrads et al. |
| 4,769,215 | A | 9/1988 | Ehrenkranz |
| 4,772,280 | A | 9/1988 | Rooyakkers |
| 4,790,830 | A | 12/1988 | Hamacher |
| 4,790,835 | A | 12/1988 | Elias |
| 4,791,686 | A | 12/1988 | Taniguchi et al. |
| 4,795,449 | A | 1/1989 | Schneider et al. |
| 4,798,603 | A | 1/1989 | Meyer et al. |
| 4,799,928 | A | 1/1989 | Crowley |
| 4,804,377 | A | 2/1989 | Hanifl et al. |
| 4,812,053 | A | 3/1989 | Bhattacharjee |
| 4,820,297 | A | 4/1989 | Kaufman et al. |
| 4,846,818 | A | 7/1989 | Keldahl et al. |
| 4,846,909 | A | 7/1989 | Klug et al. |
| 4,865,595 | A | 9/1989 | Heyden |
| 4,880,417 | A | 11/1989 | Yabrov et al. |
| 4,882,794 | A | 11/1989 | Stewart, III |
| 4,883,465 | A | 11/1989 | Brennan |
| 4,886,508 | A | 12/1989 | Washington |
| 4,886,509 | A | 12/1989 | Mattsson |
| 4,889,532 | A | 12/1989 | Metz et al. |
| 4,889,533 | A | 12/1989 | Beecher |
| 4,903,254 | A | 2/1990 | Haas |
| 4,905,692 | A | 3/1990 | More |
| 4,936,838 | A | 6/1990 | Cross et al. |
| 4,955,922 | A | 9/1990 | Terauchi |
| 4,957,487 | A | 9/1990 | Gerow |
| 4,965,460 | A | 10/1990 | Tanaka et al. |
| 4,987,849 | A | 1/1991 | Sherman |
| 5,002,541 | A | 3/1991 | Conkling et al. |
| 5,004,463 | A | 4/1991 | Nigay |
| 5,031,248 | A | 7/1991 | Kemper |
| 5,045,077 | A | 9/1991 | Blake |
| 5,045,283 | A | 9/1991 | Patel |
| 5,049,144 | A | 9/1991 | Payton |
| 5,053,339 | A | 10/1991 | Patel |
| 5,058,088 | A | 10/1991 | Haas et al. |
| 5,071,347 | A | 12/1991 | Mcguire |
| 5,078,707 | A | 1/1992 | Peter |
| 5,084,037 | A | 1/1992 | Barnett |
| 5,100,396 | A | 3/1992 | Zamierowski |

(56)                    References Cited

U.S. PATENT DOCUMENTS

| | | | |
|---|---|---|---|
| 5,112,324 A | 5/1992 | Wallace | |
| 5,147,301 A | 9/1992 | Ruvio | |
| 5,176,667 A | 1/1993 | Debring | |
| 5,195,997 A | 3/1993 | Carns | |
| 5,203,699 A | 4/1993 | Mcguire | |
| 5,244,458 A | 9/1993 | Takasu | |
| 5,246,454 A | 9/1993 | Peterson | |
| 5,267,988 A | 12/1993 | Farkas | |
| 5,275,307 A | 1/1994 | Freese | |
| 5,294,983 A | 3/1994 | Ersoz et al. | |
| 5,295,983 A | 3/1994 | Kubo | |
| 5,300,052 A | 4/1994 | Kubo | |
| 5,312,383 A | 5/1994 | Kubalak | |
| 5,318,550 A * | 6/1994 | Cermak | A61F 5/453 |
| | | | 604/350 |
| 5,340,840 A | 8/1994 | Park et al. | |
| 5,382,244 A | 1/1995 | Telang | |
| 5,409,014 A | 4/1995 | Napoli et al. | |
| 5,423,784 A | 6/1995 | Metz | |
| 5,456,246 A | 10/1995 | Schmieding et al. | |
| 5,466,229 A | 11/1995 | Elson et al. | |
| 5,478,334 A | 12/1995 | Bernstein | |
| 5,499,977 A | 3/1996 | Marx | |
| 5,543,042 A | 8/1996 | Filan et al. | |
| D373,928 S | 9/1996 | Green | |
| 5,605,161 A | 2/1997 | Cross | |
| 5,618,277 A | 4/1997 | Goulter | |
| 5,628,735 A | 5/1997 | Skow | |
| 5,636,643 A | 6/1997 | Argenta et al. | |
| 5,637,104 A | 6/1997 | Ball et al. | |
| 5,674,212 A | 10/1997 | Osborn, III et al. | |
| 5,678,564 A | 10/1997 | Lawrence et al. | |
| 5,678,654 A | 10/1997 | Uzawa | |
| 5,687,429 A | 11/1997 | Rahlff | |
| 5,695,485 A | 12/1997 | Duperret et al. | |
| 5,752,944 A | 5/1998 | Dann et al. | |
| 5,772,644 A | 6/1998 | Bark et al. | |
| 5,792,132 A | 8/1998 | Garcia | |
| 5,827,243 A | 10/1998 | Palestrant | |
| 5,827,247 A | 10/1998 | Kay | |
| 5,827,250 A | 10/1998 | Fujioka et al. | |
| 5,827,257 A | 10/1998 | Fujioka et al. | |
| D401,699 S | 11/1998 | Herchenbach et al. | |
| 5,865,378 A | 2/1999 | Hollinshead et al. | |
| 5,887,291 A | 3/1999 | Bellizzi | |
| 5,894,608 A | 4/1999 | Birbara | |
| D409,303 S | 5/1999 | Oepping | |
| 5,911,222 A | 6/1999 | Lawrence et al. | |
| 5,957,904 A | 9/1999 | Holland | |
| 5,972,505 A | 10/1999 | Phillips et al. | |
| 6,039,060 A | 3/2000 | Rower | |
| 6,050,983 A | 4/2000 | Moore et al. | |
| 6,059,762 A | 5/2000 | Boyer et al. | |
| 6,063,064 A | 5/2000 | Tuckey et al. | |
| 6,098,625 A | 8/2000 | Winkler | |
| 6,105,174 A | 8/2000 | Karlsten et al. | |
| 6,113,582 A | 9/2000 | Dwork | |
| 6,117,163 A | 9/2000 | Bierman | |
| 6,123,398 A | 9/2000 | Arai et al. | |
| 6,129,718 A | 10/2000 | Wada et al. | |
| 6,131,964 A | 10/2000 | Sareshwala | |
| 6,152,902 A | 11/2000 | Christian et al. | |
| 6,164,569 A | 12/2000 | Hollinshead et al. | |
| 6,177,606 B1 | 1/2001 | Etheredge et al. | |
| 6,209,142 B1 | 4/2001 | Mattsson et al. | |
| 6,248,096 B1 | 6/2001 | Dwork et al. | |
| 6,263,887 B1 | 7/2001 | Dunn | |
| 6,311,339 B1 | 11/2001 | Kraus | |
| 6,336,919 B1 | 1/2002 | Davis et al. | |
| 6,338,729 B1 | 1/2002 | Wada et al. | |
| 6,352,525 B1 | 3/2002 | Wakabayashi | |
| 6,394,988 B1 | 5/2002 | Hashimoto | |
| 6,398,742 B1 | 6/2002 | Kim | |
| 6,406,463 B1 | 6/2002 | Brown | |
| 6,409,712 B1 | 6/2002 | Dutari et al. | |
| 6,416,500 B1 | 7/2002 | Wada et al. | |
| 6,428,521 B1 | 8/2002 | Droll | |
| 6,475,198 B1 | 11/2002 | Lipman et al. | |
| 6,479,726 B1 | 11/2002 | Cole et al. | |
| 6,491,673 B1 | 12/2002 | Palumbo et al. | |
| 6,508,794 B1 | 1/2003 | Palumbo et al. | |
| 6,540,729 B1 | 4/2003 | Wada et al. | |
| 6,547,771 B2 | 4/2003 | Robertson et al. | |
| 6,569,133 B2 | 5/2003 | Cheng et al. | |
| D476,518 S | 7/2003 | Doppelt | |
| 6,592,560 B2 | 7/2003 | Snyder et al. | |
| 6,618,868 B2 | 9/2003 | Minnick | |
| 6,620,142 B1 | 9/2003 | Flueckiger | |
| 6,629,651 B1 | 10/2003 | Male et al. | |
| 6,635,038 B2 | 10/2003 | Scovel | |
| 6,652,495 B1 | 11/2003 | Walker | |
| 6,685,684 B1 | 2/2004 | Falconer | |
| 6,702,793 B1 | 3/2004 | Sweetser et al. | |
| 6,706,027 B2 | 3/2004 | Harvie et al. | |
| 6,732,384 B2 | 5/2004 | Scott | |
| 6,736,977 B1 | 5/2004 | Hall et al. | |
| 6,740,066 B2 | 5/2004 | Wolff et al. | |
| 6,764,477 B1 | 7/2004 | Chen et al. | |
| 6,783,519 B2 | 8/2004 | Samuelsson | |
| 6,796,974 B2 | 9/2004 | Palumbo et al. | |
| 6,814,547 B2 | 11/2004 | Childers et al. | |
| 6,849,065 B2 | 2/2005 | Schmidt et al. | |
| 6,857,137 B2 | 2/2005 | Otto | |
| 6,885,690 B2 | 4/2005 | Aggerstam et al. | |
| 6,888,044 B2 | 5/2005 | Fell et al. | |
| 6,893,425 B2 | 5/2005 | Dunn et al. | |
| 6,912,737 B2 | 7/2005 | Ernest et al. | |
| 6,918,899 B2 | 7/2005 | Harvie | |
| 6,979,324 B2 | 12/2005 | Bybordi et al. | |
| 7,018,366 B2 | 3/2006 | Easter | |
| 7,066,411 B2 | 6/2006 | Male et al. | |
| 7,122,023 B1 | 10/2006 | Hinoki | |
| 7,125,399 B2 | 10/2006 | Miskie | |
| 7,131,964 B2 | 11/2006 | Harvie | |
| 7,135,012 B2 | 11/2006 | Harvie | |
| 7,141,043 B2 | 11/2006 | Harvie | |
| D533,972 S | 12/2006 | La | |
| 7,160,273 B2 | 1/2007 | Greter et al. | |
| 7,171,699 B2 | 2/2007 | Ernest et al. | |
| 7,171,871 B2 | 2/2007 | Kozak | |
| 7,179,951 B2 | 2/2007 | Krishnaswamy-mirle et al. | |
| 7,181,781 B1 | 2/2007 | Trabold et al. | |
| 7,186,245 B1 | 3/2007 | Cheng et al. | |
| 7,192,424 B2 | 3/2007 | Cooper | |
| 7,220,250 B2 | 5/2007 | Suzuki et al. | |
| D562,975 S | 2/2008 | Otto | |
| 7,335,189 B2 | 2/2008 | Harvie | |
| 7,358,282 B2 | 4/2008 | Krueger et al. | |
| 7,390,320 B2 | 6/2008 | Machida et al. | |
| 7,438,706 B2 | 10/2008 | Koizumi et al. | |
| 7,488,310 B2 | 2/2009 | Yang | |
| 7,491,194 B1 | 2/2009 | Oliwa | |
| D591,106 S | 4/2009 | Dominique et al. | |
| 7,513,381 B2 | 4/2009 | Heng et al. | |
| 7,520,872 B2 | 4/2009 | Biggie et al. | |
| D593,801 S | 6/2009 | Wilson et al. | |
| 7,540,364 B2 | 6/2009 | Sanderson | |
| 7,585,293 B2 | 9/2009 | Vermaak | |
| 7,588,560 B1 | 9/2009 | Dunlop | |
| 7,665,359 B2 | 2/2010 | Barber | |
| 7,682,347 B2 | 3/2010 | Parks et al. | |
| 7,687,004 B2 | 3/2010 | Allen | |
| 7,695,459 B2 | 4/2010 | Gilbert et al. | |
| 7,695,460 B2 | 4/2010 | Wada et al. | |
| 7,699,818 B2 | 4/2010 | Gilbert | |
| 7,699,831 B2 | 4/2010 | Bengtson et al. | |
| 7,722,584 B2 | 5/2010 | Tanaka et al. | |
| 7,727,206 B2 | 6/2010 | Gorres | |
| 7,740,620 B2 | 6/2010 | Gilbert et al. | |
| 7,749,205 B2 | 7/2010 | Tazoe et al. | |
| 7,755,497 B2 | 7/2010 | Wada et al. | |
| 7,766,887 B2 | 8/2010 | Burns, Jr. et al. | |
| D625,407 S | 10/2010 | Koizumi et al. | |
| 7,806,879 B2 | 10/2010 | Brooks et al. | |

(56) References Cited

U.S. PATENT DOCUMENTS

| | | |
|---|---|---|
| 7,811,272 B2 | 10/2010 | Lindsay et al. |
| 7,815,067 B2 | 10/2010 | Matsumoto et al. |
| 7,833,169 B2 | 11/2010 | Hannon |
| 7,857,806 B2 | 12/2010 | Karpowicz et al. |
| 7,866,942 B2 | 1/2011 | Harvie |
| 7,871,385 B2 | 1/2011 | Levinson et al. |
| 7,875,010 B2 | 1/2011 | Frazier et al. |
| 7,901,389 B2 | 3/2011 | Mombrinie |
| 7,927,320 B2 | 4/2011 | Goldwasser et al. |
| 7,927,321 B2 | 4/2011 | Marland |
| 7,931,634 B2 | 4/2011 | Swiecicki et al. |
| 7,939,706 B2 | 5/2011 | Okabe et al. |
| 7,946,443 B2 | 5/2011 | Stull et al. |
| 7,947,025 B2 | 5/2011 | Buglino et al. |
| 7,963,419 B2 | 6/2011 | Burney et al. |
| 7,976,519 B2 | 7/2011 | Bubb et al. |
| 7,993,318 B2 | 8/2011 | Olsson et al. |
| 8,015,627 B2 | 9/2011 | Baker et al. |
| 8,028,460 B2 | 10/2011 | Williams |
| 8,047,398 B2 | 11/2011 | Dimartino et al. |
| 8,083,094 B2 | 12/2011 | Caulfield et al. |
| 8,128,608 B2 | 3/2012 | Thevenin |
| 8,181,651 B2 | 5/2012 | Pinel |
| 8,181,819 B2 | 5/2012 | Burney et al. |
| 8,211,063 B2 | 7/2012 | Bierman et al. |
| 8,221,369 B2 | 7/2012 | Parks et al. |
| 8,241,262 B2 | 8/2012 | Mahnensmith |
| 8,277,426 B2 | 10/2012 | Wilcox et al. |
| 8,287,508 B1 | 10/2012 | Sanchez |
| 8,303,554 B2 | 11/2012 | Tsai et al. |
| 8,322,565 B2 | 12/2012 | Caulfield et al. |
| 8,337,477 B2 | 12/2012 | Parks et al. |
| D674,241 S | 1/2013 | Bickert et al. |
| 8,343,122 B2 | 1/2013 | Gorres |
| 8,353,074 B2 | 1/2013 | Krebs |
| 8,353,886 B2 | 1/2013 | Bester et al. |
| D676,241 S | 2/2013 | Merrill |
| 8,388,588 B2 | 3/2013 | Wada et al. |
| D679,807 S | 4/2013 | Burgess et al. |
| 8,425,482 B2 | 4/2013 | Khoubnazar |
| 8,449,510 B2 | 5/2013 | Martini et al. |
| D684,260 S | 6/2013 | Lund et al. |
| 8,470,230 B2 | 6/2013 | Caulfield et al. |
| 8,479,941 B2 | 7/2013 | Matsumoto et al. |
| 8,479,949 B2 | 7/2013 | Henkel |
| 8,500,719 B1 | 8/2013 | Simpson et al. |
| 8,512,301 B2 | 8/2013 | Ma |
| 8,529,530 B2 | 9/2013 | Koch et al. |
| 8,535,284 B2 | 9/2013 | Joder et al. |
| 8,546,639 B2 | 10/2013 | Wada et al. |
| 8,551,075 B2 | 10/2013 | Bengtson |
| 8,568,376 B2 | 10/2013 | Delattre et al. |
| D694,404 S | 11/2013 | Burgess et al. |
| 8,585,683 B2 | 11/2013 | Bengtson et al. |
| 8,586,583 B2 | 11/2013 | Hamblin et al. |
| 8,652,112 B2 | 2/2014 | Johannison et al. |
| D702,973 S | 4/2014 | Norland et al. |
| 8,703,032 B2 | 4/2014 | Menon et al. |
| D704,330 S | 5/2014 | Cicatelli |
| D704,510 S | 5/2014 | Mason et al. |
| D705,423 S | 5/2014 | Walsh Cutler |
| D705,926 S | 5/2014 | Burgess et al. |
| 8,714,394 B2 | 5/2014 | Wulf |
| 8,715,267 B2 | 5/2014 | Bengtson et al. |
| 8,757,425 B2 | 6/2014 | Copeland |
| 8,777,032 B2 | 7/2014 | Biesecker et al. |
| 8,808,260 B2 | 8/2014 | Koch et al. |
| 8,864,730 B2 | 10/2014 | Conway et al. |
| 8,881,923 B2 | 11/2014 | Higginson |
| 8,882,731 B2 | 11/2014 | Suzuki et al. |
| 8,936,585 B2 | 1/2015 | Carson et al. |
| D729,581 S | 5/2015 | Boroski |
| 9,028,460 B2 | 5/2015 | Medeiros |
| 9,056,698 B2 | 6/2015 | Noer |
| 9,078,792 B2 | 7/2015 | Ruiz |
| 9,173,602 B2 | 11/2015 | Gilbert |
| 9,173,799 B2 | 11/2015 | Tanimoto et al. |
| 9,187,220 B2 | 11/2015 | Biesecker et al. |
| 9,199,772 B2 | 12/2015 | Krippendorf |
| 9,233,020 B2 | 1/2016 | Matsumiya |
| 9,248,058 B2 | 2/2016 | Conway et al. |
| 9,308,118 B1 | 4/2016 | Dupree et al. |
| 9,309,029 B2 | 4/2016 | Incorvia et al. |
| 9,333,281 B2 | 5/2016 | Giezendanner et al. |
| 9,382,047 B2 | 7/2016 | Schmidtner et al. |
| 9,456,937 B2 | 10/2016 | Ellis |
| 9,480,595 B2 | 11/2016 | Baham et al. |
| 9,517,865 B2 | 12/2016 | Albers et al. |
| D777,941 S | 1/2017 | Piramoon |
| 9,533,806 B2 | 1/2017 | Ding et al. |
| 9,550,611 B2 | 1/2017 | Hodge |
| 9,555,930 B2 | 1/2017 | Campbell et al. |
| 9,623,159 B2 | 4/2017 | Locke |
| D789,522 S | 6/2017 | Burgess et al. |
| 9,687,849 B2 | 6/2017 | Bruno et al. |
| 9,694,949 B2 | 7/2017 | Hendricks et al. |
| 9,713,547 B2 | 7/2017 | Lee et al. |
| 9,788,992 B2 | 10/2017 | Harvie |
| D804,907 S | 12/2017 | Sandoval |
| 9,868,564 B2 | 1/2018 | Mcgirr et al. |
| D814,239 S | 4/2018 | Arora |
| D817,484 S | 5/2018 | Lafond |
| 10,037,640 B2 | 7/2018 | Gordon |
| 10,058,470 B2 | 8/2018 | Phillips |
| 10,098,990 B2 | 10/2018 | Koch et al. |
| D835,264 S | 12/2018 | Mozzicato et al. |
| D835,779 S | 12/2018 | Mozzicato et al. |
| D840,533 S | 2/2019 | Mozzicato et al. |
| D840,534 S | 2/2019 | Mozzicato et al. |
| 10,225,376 B2 | 3/2019 | Perez Martinez |
| 10,226,376 B2 | 3/2019 | Sanchez et al. |
| D848,612 S | 5/2019 | Mozzicato et al. |
| 10,307,305 B1 | 6/2019 | Hodges |
| 10,335,121 B2 | 7/2019 | Desai |
| D856,512 S | 8/2019 | Cowart et al. |
| 10,376,406 B2 | 8/2019 | Newton |
| 10,376,407 B2 | 8/2019 | Newton |
| 10,390,989 B2 | 8/2019 | Sanchez et al. |
| D858,144 S | 9/2019 | Fu |
| 10,406,039 B2 | 9/2019 | Villarreal |
| 10,407,222 B2 | 9/2019 | Allen |
| 10,478,356 B2 | 11/2019 | Griffin |
| 10,538,366 B2 | 1/2020 | Pentelovitch et al. |
| 10,569,938 B2 | 2/2020 | Zhao et al. |
| 10,577,156 B2 | 3/2020 | Dagnelie et al. |
| 10,618,721 B2 | 4/2020 | Vazin |
| D884,390 S | 5/2020 | Wang |
| 10,669,079 B2 | 6/2020 | Freedman et al. |
| D892,315 S | 8/2020 | Airy |
| 10,730,672 B2 | 8/2020 | Bertram et al. |
| 10,737,848 B2 | 8/2020 | Philip et al. |
| 10,765,854 B2 | 9/2020 | Law et al. |
| 10,766,670 B2 | 9/2020 | Kittmann |
| 10,799,386 B1 | 10/2020 | Harrison |
| D901,214 S | 11/2020 | Hu |
| 10,857,025 B2 | 12/2020 | Davis et al. |
| 10,865,017 B1 | 12/2020 | Cowart et al. |
| 10,889,412 B2 | 1/2021 | West et al. |
| 10,913,581 B2 | 2/2021 | Stahlecker |
| D912,244 S | 3/2021 | Rehm et al. |
| 10,952,889 B2 | 3/2021 | Newton et al. |
| 10,973,678 B2 | 4/2021 | Newton et al. |
| 10,974,874 B2 | 4/2021 | Ragias et al. |
| 11,000,401 B2 | 5/2021 | Ecklund et al. |
| D923,365 S | 6/2021 | Wang |
| 11,026,829 B2 | 6/2021 | Harvie |
| 11,027,900 B2 | 6/2021 | Liu |
| 11,045,346 B2 | 6/2021 | Argent et al. |
| D928,946 S | 8/2021 | Sanchez et al. |
| 11,179,506 B2 | 11/2021 | Barr et al. |
| 11,226,376 B2 | 1/2022 | Yamauchi et al. |
| 11,376,152 B2 | 7/2022 | Sanchez et al. |
| 11,382,786 B2 | 7/2022 | Sanchez et al. |
| 11,382,788 B2 | 7/2022 | Hjorth et al. |

(56) References Cited

U.S. PATENT DOCUMENTS

| | | |
|---|---|---|
| 11,426,303 B2 | 8/2022 | Davis et al. |
| 11,529,252 B2 | 12/2022 | Glithero et al. |
| 2001/0037097 A1 | 11/2001 | Cheng et al. |
| 2001/0054426 A1 | 12/2001 | Knudson et al. |
| 2002/0019614 A1 | 2/2002 | Woon |
| 2002/0026161 A1 | 2/2002 | Grundke |
| 2002/0087131 A1 | 7/2002 | Wolff et al. |
| 2002/0091364 A1 | 7/2002 | Prabhakar |
| 2002/0189992 A1 | 12/2002 | Schmidt et al. |
| 2002/0193760 A1 | 12/2002 | Thompson |
| 2003/0004436 A1 | 1/2003 | Schmidt et al. |
| 2003/0032931 A1 | 2/2003 | Grundke et al. |
| 2003/0120178 A1 | 6/2003 | Heki |
| 2003/0157859 A1 | 8/2003 | Ishikawa |
| 2003/0181880 A1 | 9/2003 | Schwartz |
| 2003/0195484 A1 | 10/2003 | Harvie |
| 2003/0204173 A1 | 10/2003 | Burns et al. |
| 2003/0233079 A1 | 12/2003 | Parks et al. |
| 2004/0006321 A1 | 1/2004 | Cheng et al. |
| 2004/0056122 A1 | 3/2004 | Male et al. |
| 2004/0084465 A1 | 5/2004 | Luburic |
| 2004/0127872 A1 | 7/2004 | Petryk et al. |
| 2004/0128749 A1 | 7/2004 | Scott |
| 2004/0143229 A1 | 7/2004 | Easter |
| 2004/0147894 A1 | 7/2004 | Mizutani et al. |
| 2004/0158221 A1 | 8/2004 | Mizutani et al. |
| 2004/0176731 A1 | 9/2004 | Cheng et al. |
| 2004/0191919 A1 | 9/2004 | Unger et al. |
| 2004/0207530 A1 | 10/2004 | Nielsen |
| 2004/0236292 A1 | 11/2004 | Tazoe et al. |
| 2004/0254547 A1 | 12/2004 | Okabe et al. |
| 2005/0010182 A1 | 1/2005 | Parks et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0273920 A1 | 12/2005 | Marinas |
| 2005/0277904 A1 | 12/2005 | Chase et al. |
| 2005/0279359 A1 | 12/2005 | LeBlanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0079854 A1 | 4/2006 | Kay et al. |
| 2006/0111648 A1 | 5/2006 | Vermaak |
| 2006/0155214 A1 | 7/2006 | Wightman |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0135786 A1 | 6/2007 | Schmidt et al. |
| 2007/0149935 A1 | 6/2007 | Dirico |
| 2007/0191804 A1 | 8/2007 | Coley |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0281282 A1 | 11/2008 | Finger et al. |
| 2008/0287894 A1 | 11/2008 | Van Den Heuvel et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0264840 A1 | 10/2009 | Virginio |
| 2009/0270822 A1 | 10/2009 | Medeiros |
| 2009/0281510 A1 | 11/2009 | Fisher |
| 2010/0004612 A1 | 1/2010 | Thevenin |
| 2010/0058660 A1 | 3/2010 | Williams |
| 2010/0121289 A1 | 5/2010 | Parks et al. |
| 2010/0158168 A1 | 6/2010 | Murthy et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |

(56) References Cited

U.S. PATENT DOCUMENTS

| | | |
|---|---|---|
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0150813 A1 | 6/2013 | Gordon et al. |
| 2013/0245496 A1 | 9/2013 | Wells et al. |
| 2013/0245586 A1 | 9/2013 | Jha |
| 2013/0292537 A1 | 11/2013 | Dirico |
| 2014/0031774 A1 | 1/2014 | Bengtson |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0367726 A1 | 12/2016 | Gratzer |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042748 A1 | 2/2017 | Griffin |
| 2017/0100276 A1 | 4/2017 | Joh |
| 2017/0128638 A1 | 5/2017 | Giezendanner et al. |
| 2017/0143534 A1 | 5/2017 | Sanchez |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0247222 A1 | 8/2019 | Ecklund et al. |
| 2019/0247223 A1 | 8/2019 | Brun et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2020/0008985 A1 | 1/2020 | Nguyen et al. |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085610 A1 | 3/2020 | Cohn et al. |
| 2020/0086090 A1 | 3/2020 | Von Weymarn-Schärli et al. |
| 2020/0129322 A1 | 4/2020 | Leuckel |
| 2020/0171217 A9 | 6/2020 | Braga et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315838 A1 | 10/2020 | Eckert |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0267787 A1 | 9/2021 | Nazemi |
| 2021/0275343 A1 | 9/2021 | Sanchez et al. |
| 2021/0315727 A1 | 10/2021 | Jiang |
| 2021/0353450 A1 | 11/2021 | Sharma et al. |

(56)  References Cited

U.S. PATENT DOCUMENTS

| | | | |
|---|---|---|---|
| 2021/0361469 | A1 | 11/2021 | Liu et al. |
| 2021/0369495 | A1 | 12/2021 | Cheng et al. |
| 2021/0386925 | A1 | 12/2021 | Hartwell et al. |
| 2021/0393433 | A1 | 12/2021 | Godinez et al. |
| 2022/0023091 | A1 | 1/2022 | Ecklund et al. |
| 2022/0047410 | A1 | 2/2022 | Walthall |
| 2022/0062027 | A1 | 3/2022 | Mitchell et al. |
| 2022/0062028 | A1 | 3/2022 | Mitchell et al. |
| 2022/0062029 | A1 | 3/2022 | Johannes et al. |
| 2022/0066825 | A1 | 3/2022 | Saraf et al. |
| 2022/0071811 | A1 | 3/2022 | Cheng et al. |
| 2022/0071826 | A1 | 3/2022 | Kulkarni et al. |
| 2022/0104965 | A1 | 4/2022 | Vaninetti et al. |
| 2022/0104981 | A1 | 4/2022 | Jones |
| 2022/0117774 | A1 | 4/2022 | Meyer et al. |
| 2022/0117775 | A1 | 4/2022 | Jones et al. |
| 2022/0133524 | A1 | 5/2022 | Davis |
| 2022/0151817 | A1 | 5/2022 | Mann |
| 2022/0160949 | A1 | 5/2022 | Simiele et al. |
| 2022/0218510 | A1 | 7/2022 | Metzger et al. |
| 2022/0229053 | A1 | 7/2022 | Levin et al. |
| 2022/0248836 | A1 | 8/2022 | Cagle et al. |
| 2022/0257407 | A1 | 8/2022 | Johannes et al. |
| 2022/0265462 | A1 | 8/2022 | Alder et al. |
| 2022/0273482 | A1 | 9/2022 | Johannes et al. |
| 2022/0280357 | A1 | 9/2022 | Jagannathan et al. |
| 2022/0313222 | A1 | 10/2022 | Austermann et al. |
| 2022/0313474 | A1 | 10/2022 | Kriscovich et al. |
| 2022/0354685 | A1 | 11/2022 | Davis et al. |
| 2022/0370231 | A1 | 11/2022 | Wang et al. |
| 2022/0370234 | A1 | 11/2022 | Hughett et al. |
| 2022/0370235 | A1 | 11/2022 | Johannes et al. |
| 2022/0370237 | A1 | 11/2022 | Parmar et al. |
| 2022/0387001 | A1 | 12/2022 | Askenazi et al. |
| 2022/0395391 | A1 | 12/2022 | Saunders et al. |
| 2023/0018845 | A1 | 1/2023 | Lee |
| 2023/0020563 | A1 | 1/2023 | Sharma et al. |
| 2023/0031640 | A1 | 2/2023 | Hughett et al. |
| 2023/0037159 | A1 | 2/2023 | Brennan et al. |
| 2023/0062944 | A1 | 3/2023 | Vollenberg et al. |
| 2023/0062994 | A1 | 3/2023 | Ecklund et al. |
| 2023/0089032 | A1 | 3/2023 | Hughett et al. |
| 2023/0105001 | A1 | 4/2023 | Whittome et al. |
| 2023/0138269 | A1 | 5/2023 | Abdelal et al. |
| 2023/0145365 | A1 | 5/2023 | Martin et al. |
| 2023/0277362 | A1 | 9/2023 | Davis et al. |

FOREIGN PATENT DOCUMENTS

| | | | |
|---|---|---|---|
| CA | 2354132 | A1 | 6/2000 |
| CA | 2488867 | C | 8/2007 |
| CA | 3050918 | A1 | 8/2018 |
| CA | 3098571 | A1 | 11/2019 |
| CN | 2269203 | Y | 12/1997 |
| CN | 1332620 | A | 1/2002 |
| CN | 1533755 | A | 10/2004 |
| CN | 1602825 | A | 4/2005 |
| CN | 1720888 | A | 1/2006 |
| CN | 2936204 | Y | 8/2007 |
| CN | 101262836 | A | 9/2008 |
| CN | 101522148 | A | 9/2009 |
| CN | 102159159 | A | 8/2011 |
| CN | 202184840 | U | 4/2012 |
| CN | 102481441 | A | 5/2012 |
| CN | 202463712 | U | 10/2012 |
| CN | 103533968 | A | 1/2014 |
| CN | 103717180 | A | 4/2014 |
| CN | 204562697 | U | 8/2015 |
| CN | 105451693 | A | 3/2016 |
| CN | 205849719 | U | 1/2017 |
| CN | 107847384 | A | 3/2018 |
| CN | 107920912 | A | 4/2018 |
| CN | 209285902 | U | 8/2019 |
| CN | 110381883 | A | 10/2019 |
| CN | 211198839 | U | 8/2020 |
| CN | 112566550 | A | 3/2021 |
| CN | 112603184 | A | 4/2021 |
| CN | 114007493 | A | 2/2022 |
| CN | 114375187 | A | 4/2022 |
| CN | 116096332 | A | 5/2023 |
| DE | 79818 | C | 10/1893 |
| DE | 1516466 | A1 | 6/1969 |
| DE | 2721330 | A1 | 11/1977 |
| DE | 2742298 | A1 | 3/1978 |
| DE | 9407554.9 | U1 | 5/1995 |
| DE | 4443710 | A1 | 6/1995 |
| DE | 19619597 | A1 | 11/1997 |
| DE | 102011103783 | A1 | 12/2012 |
| DE | 202015104597 | U1 | 7/2016 |
| DK | 9600118 | | 11/1996 |
| EP | 0032138 | A2 | 7/1981 |
| EP | 0066070 | B1 | 12/1982 |
| EP | 0274753 | A2 | 7/1988 |
| EP | 0119143 | B1 | 11/1988 |
| EP | 0610638 | A1 | 8/1994 |
| EP | 0613355 | A1 | 9/1994 |
| EP | 0613355 | B1 | 1/1997 |
| EP | 0787472 | A1 | 8/1997 |
| EP | 0966936 | A1 | 12/1999 |
| EP | 0987293 | A1 | 3/2000 |
| EP | 1063953 | A1 | 1/2001 |
| EP | 0653928 | B1 | 10/2002 |
| EP | 1332738 | A1 | 8/2003 |
| EP | 1382318 | A1 | 1/2004 |
| EP | 1089684 | B1 | 10/2004 |
| EP | 1616542 | A1 | 1/2006 |
| EP | 1382318 | B1 | 5/2006 |
| EP | 1063953 | B1 | 1/2007 |
| EP | 1872752 | A1 | 1/2008 |
| EP | 2180907 | A1 | 5/2010 |
| EP | 2380532 | A1 | 10/2011 |
| EP | 2389908 | A1 | 11/2011 |
| EP | 2601916 | A1 | 6/2013 |
| EP | 2676643 | A1 | 12/2013 |
| EP | 2997950 | A2 | 3/2016 |
| EP | 2879534 | B1 | 3/2017 |
| EP | 3424471 | A1 | 1/2019 |
| EP | 3169292 | B1 | 11/2019 |
| EP | 3753492 | A1 | 12/2020 |
| EP | 3788992 | A1 | 3/2021 |
| EP | 3576689 | B1 | 3/2022 |
| EP | 3752110 | B1 | 3/2022 |
| EP | 4025163 | A1 | 7/2022 |
| GB | 1011517 | A | 12/1965 |
| GB | 1467144 | A | 3/1977 |
| GB | 2106395 | A | 4/1983 |
| GB | 2106784 | A | 4/1983 |
| GB | 2148126 | A | 5/1985 |
| GB | 2171315 | A | 8/1986 |
| GB | 2148126 | B | 7/1987 |
| GB | 2191095 | A | 12/1987 |
| GB | 2199750 | A | 7/1988 |
| GB | 2260907 | A | 5/1993 |
| GB | 2462267 | A | 2/2010 |
| GB | 2469496 | A | 10/2010 |
| GB | 2490327 | A | 10/2012 |
| GB | 2507318 | A | 4/2014 |
| IT | 201800009129 | A1 | 4/2020 |
| JP | S5410596 | A | 1/1979 |
| JP | S5410596 | Y2 | 5/1979 |
| JP | S55155618 | A | 12/1980 |
| JP | H0267530 | A | 3/1990 |
| JP | H02103871 | A | 4/1990 |
| JP | H02131422 | A | 5/1990 |
| JP | H02131422 | U | 11/1990 |
| JP | H0460220 | A | 2/1992 |
| JP | H04060220 | U | 2/1992 |
| JP | H05123349 | A | 5/1993 |
| JP | H05123350 | A | 5/1993 |
| JP | H085630 | A | 1/1996 |
| JP | H1040141 | A | 2/1998 |
| JP | H10225430 | A | 8/1998 |
| JP | H11113946 | A | 4/1999 |
| JP | H11290365 | A | 10/1999 |

(56) References Cited

FOREIGN PATENT DOCUMENTS

| | | | |
|---|---|---|---|
| JP | 2000116690 A | 4/2000 |
| JP | 2000185068 A | 7/2000 |
| JP | 3087938 B2 | 9/2000 |
| JP | 2001054531 A | 2/2001 |
| JP | 2001070331 A | 3/2001 |
| JP | 2001276107 A | 10/2001 |
| JP | 2001276108 A | 10/2001 |
| JP | 2002028173 A | 1/2002 |
| JP | 2003505152 A | 2/2003 |
| JP | 2003180722 A | 7/2003 |
| JP | 2004130056 A | 4/2004 |
| JP | 2004267530 A | 9/2004 |
| JP | 2005066011 A | 3/2005 |
| JP | 2005066325 A | 3/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 4039641 B2 | 11/2007 |
| JP | 2009509570 A | 3/2009 |
| JP | 2010081981 A | 4/2010 |
| JP | 4640772 B2 | 12/2010 |
| JP | 2010536439 A | 12/2010 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 2012523869 A | 10/2012 |
| JP | 2013238608 A | 11/2013 |
| JP | 2014521960 A | 8/2014 |
| JP | 2015092945 A | 5/2015 |
| JP | 3198994 B2 | 7/2015 |
| JP | 2019525811 A | 9/2019 |
| JP | 2021120686 A | 8/2021 |
| JP | 2021522009 A | 8/2021 |
| JP | 7129493 B2 | 8/2022 |
| KR | 200290061 Y1 * | 5/2002 |
| KR | 20030047451 A | 6/2003 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | WO-03055423 A1 * | 7/2003 | ........... A61F 5/4405 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |
| WO | 2015170307 A1 | 11/2015 |
| WO | 2015197462 A1 | 12/2015 |
| WO | 2016051385 A1 | 4/2016 |
| WO | 2016055989 A1 | 4/2016 |
| WO | 2016071894 A1 | 5/2016 |
| WO | 2016103242 A1 | 6/2016 |
| WO | 2016116915 A1 | 7/2016 |
| WO | 2016124203 A1 | 8/2016 |
| WO | 2016139448 A1 | 9/2016 |
| WO | 2016166562 A1 | 10/2016 |
| WO | 2016167535 A1 | 10/2016 |
| WO | 2016191574 A1 | 12/2016 |
| WO | 2016200088 A1 | 12/2016 |
| WO | 2016200361 A1 | 12/2016 |
| WO | 2016204731 A1 | 12/2016 |
| WO | 2017001846 A1 | 1/2017 |
| WO | 2017075226 A1 | 5/2017 |
| WO | 2017152198 A1 | 9/2017 |
| WO | 2017162559 A1 | 9/2017 |
| WO | WO-2017153357 A1 * | 9/2017 | ....... A61F 13/00068 |
| WO | 2017205446 A1 | 11/2017 |
| WO | 2017209779 A1 | 12/2017 |

(56)         References Cited

FOREIGN PATENT DOCUMENTS

| WO | 2017210524 A1 | 12/2017 |
| WO | 2018022414 A1 | 2/2018 |
| WO | 2018044781 A1 | 3/2018 |
| WO | 2018056953 A1 | 3/2018 |
| WO | 2018090550 A1 | 5/2018 |
| WO | 2018138513 A1 | 8/2018 |
| WO | 2018144318 A1 | 8/2018 |
| WO | 2018144463 A1 | 8/2018 |
| WO | 2018150263 A1 | 8/2018 |
| WO | 2018150268 A1 | 8/2018 |
| WO | 2018152156 A1 | 8/2018 |
| WO | 2018183791 A1 | 10/2018 |
| WO | 2018150267 A3 | 11/2018 |
| WO | 2018235026 A1 | 12/2018 |
| WO | 2018235065 A1 | 12/2018 |
| WO | 2019004404 A1 | 1/2019 |
| WO | 2019065541 A1 | 4/2019 |
| WO | 2019096845 A1 | 5/2019 |
| WO | 2019150385 A1 | 8/2019 |
| WO | 2019161094 A1 | 8/2019 |
| WO | 2019188566 A1 | 10/2019 |
| WO | 2019190593 A1 | 10/2019 |
| WO | 2019212949 A1 | 11/2019 |
| WO | 2019212950 A1 | 11/2019 |
| WO | 2019212951 A1 | 11/2019 |
| WO | 2019212952 A1 | 11/2019 |
| WO | 2019212954 A1 | 11/2019 |
| WO | 2019212955 A1 | 11/2019 |
| WO | 2019212956 A1 | 11/2019 |
| WO | 2019214787 A1 | 11/2019 |
| WO | 2019214788 A1 | 11/2019 |
| WO | 2020000994 A1 | 1/2020 |
| WO | 2020020618 A1 | 1/2020 |
| WO | 2020038822 A1 | 2/2020 |
| WO | 2020088409 A1 | 5/2020 |
| WO | 2020049394 A3 | 6/2020 |
| WO | 2020120657 A1 | 6/2020 |
| WO | 2020152575 A1 | 7/2020 |
| WO | 2020182923 A1 | 9/2020 |
| WO | 2020204967 A1 | 10/2020 |
| WO | 2020209898 A1 | 10/2020 |
| WO | 2020242790 A1 | 12/2020 |
| WO | 2020251893 A1 | 12/2020 |
| WO | 2020256865 A1 | 12/2020 |
| WO | 2021007144 A1 | 1/2021 |
| WO | 2021007345 A1 | 1/2021 |
| WO | 2021010844 A1 | 1/2021 |
| WO | 2021016026 A1 | 1/2021 |
| WO | 2021016300 A1 | 1/2021 |
| WO | 2021025919 A1 | 2/2021 |
| WO | 2021034886 A1 | 2/2021 |
| WO | 2021041123 A1 | 3/2021 |
| WO | 2021086868 A1 | 5/2021 |
| WO | 2021094352 A1 | 5/2021 |
| WO | 2021094639 A1 | 5/2021 |
| WO | 2021102296 A1 | 5/2021 |
| WO | 2021138411 A1 | 7/2021 |
| WO | 2021138414 A1 | 7/2021 |
| WO | 2021155206 A1 | 8/2021 |
| WO | 2021173436 A1 | 9/2021 |
| WO | 2021195384 A1 | 9/2021 |
| WO | 2021207621 A1 | 10/2021 |
| WO | 2021211568 A1 | 10/2021 |
| WO | 2021216419 A1 | 10/2021 |
| WO | 2021216422 A1 | 10/2021 |
| WO | 2021247523 A1 | 12/2021 |
| WO | 2021257202 A1 | 12/2021 |
| WO | 2022006256 A1 | 1/2022 |
| WO | 2022031943 A1 | 2/2022 |
| WO | 2022035745 A1 | 2/2022 |
| WO | 2022076427 A2 | 4/2022 |
| WO | 2022086898 A1 | 4/2022 |
| WO | 2022098536 A1 | 5/2022 |
| WO | 2022125685 A1 | 6/2022 |
| WO | 2022140545 A1 | 6/2022 |
| WO | 2022150360 A1 | 7/2022 |
| WO | 2022150463 A1 | 7/2022 |
| WO | 2022159392 A1 | 7/2022 |
| WO | 2022170182 A1 | 8/2022 |
| WO | 2022182385 A1 | 9/2022 |
| WO | 2022192188 A1 | 9/2022 |
| WO | 2022192347 A1 | 9/2022 |
| WO | 2023014641 A1 | 2/2023 |
| WO | 2023034453 A1 | 3/2023 |
| WO | 2023038945 A1 | 3/2023 |
| WO | 2023038950 A1 | 3/2023 |
| WO | 2023049175 A1 | 3/2023 |
| WO | 2023086394 A1 | 5/2023 |
| WO | 2023191764 A1 | 10/2023 |

OTHER PUBLICATIONS

Final Office Action for U.S. Appl. No. 14/952,591 mailed Nov. 27, 2020.
Non-Final Office Action for U.S. Appl. No. 16/904,868 mailed Nov. 25, 2020.
Non-Final Office Action for U.S. Appl. No. 16/905,400 mailed Dec. 2, 2020.
Non-Final Office Action for U.S. Appl. No. 17/088,272 mailed Jan. 25, 2021.
Notice of Allowance for U.S. Appl. No. 15/171,968 mailed Nov. 6, 2020.
Notice of Allowance for U.S. Appl. No. 15/612,325 mailed Jan. 21, 2021.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 63/134,287, filed Jan. 6, 2021.
U.S. Appl. No. 63/134,632, filed Jan. 7, 2021.
Sage's Second Supplemental Invalidity Contentions Regarding U.S. Pat. Nos. 8,287,508, 10,226,375, 10,390,989, and 10,376,407, 292 pages.
"AMXD Control Starter Kit Brochure", https://www.omnimedicalsys.com/index.php?page=products, Omni Medical, 8 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, MD&DI, 2014, 4 pages.
Newton, et al., "Measuring Safety, Effectiveness and Ease of Use of PureWick in the Management of Urinary Incontinence in Bedbound Women: Case Studies", Jan. 8, 2016, 11 pages.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
AMXDmax In-Flight Bladder Relief; Omni Medical 2015; Omni Medical Systems, Inc.
Corrected International Search Report and Written Opinion for International Application No. PCT/US2017/043025 mailed Jan. 11, 2018.

(56) References Cited

OTHER PUBLICATIONS

Corrected Notice of Allowability for U.S. Appl. No. 15/221,106 mailed Jul. 2, 2019.

Final Office Action for U.S. Appl. No. 14/722,613 mailed on Nov. 29, 2018.

Final Office Action for U.S. Appl. No. 14/947,759 mailed Apr. 8, 2016.

Final Office Action for U.S. Appl. No. 14/952,591 mailed Feb. 23, 2018.

Final Office Action for U.S. Appl. No. 14/952,591 mailed Nov. 1, 2019.

Final Office Action for U.S. Appl. No. 15/171,968 mailed Feb. 14, 2020.

Final Office Action for U.S. Appl. No. 15/171,968 mailed Mar. 19, 2019.

Final Office Action for U.S. Appl. No. 15/221,106 mailed Jan. 23, 2019.

Final Office Action for U.S. Appl. No. 15/238,427 mailed Jan. 2, 2019.

Final Office Action for U.S. Appl. No. 15/260,103 mailed Feb. 14, 2019.

Final Office Action for U.S. Appl. No. 15/612,325 mailed Sep. 17, 2020.

Final Office Action for U.S. Appl. No. 29/624,661 mailed Feb. 18, 2020.

International Search Report and Written Opinion from International Application No. PCT/US2016/049274 mailed Dec. 1, 2016.

International Search Report and Written Opinion from International Application No. PCT/US2017/035625 mailed Aug. 15, 2017.

International Search Report and Written Opinion from International Application No. PCT/US2017/043025 mailed Oct. 18, 2017.

International Search Report and Written Opinion from International Application No. PCT/US2018/015968 mailed Apr. 6, 2018.

International Search Report and Written Opinion from International Application No. PCT/US2019/029608 mailed Sep. 3, 2019.

International Search Report and Written Opinion from International Application No. PCT/US2019/029609 mailed Sep. 3, 2019.

International Search Report and Written Opinion from International Application No. PCT/US2019/029610 mailed Sep. 3, 2019.

International Search Report and Written Opinion from International Application No. PCT/US2019/029611 mailed Jul. 3, 2019.

International Search Report and Written Opinion from International Application No. PCT/US2019/029613 mailed Jul. 3, 2019.

International Search Report and Written Opinion from International Application No. PCT/US2019/029614 mailed Sep. 26, 2019.

International Search Report and Written Opinion from International Application No. PCT/US2019/029616 mailed Aug. 30, 2019.

International Search Report and Written Opinion from International Application No. PCT/US2020/023572 mailed Jul. 6, 2020.

Issue Notification for U.S. Appl. No. 15/221,106 mailed Jul. 24, 2019.

Issue Notification for U.S. Appl. No. 15/238,427 mailed Jul. 24, 2019.

Issue Notification for U.S. Appl. No. 15/260,103 mailed Aug. 7, 2019.

Issue Notification for U.S. Appl. No. 15/611,587 mailed Feb. 20, 2019.

Non-Final Office Action for U.S. Appl. No. 14/592,591 mailed Mar. 20, 2020.

Non-Final Office Action for U.S. Appl. No. 14/722,613 mailed Jun. 13, 2019.

Non-Final Office Action for U.S. Appl. No. 14/947,759, mailed Mar. 17, 2016.

Non-Final Office Action for U.S. Appl. No. 14/952,591 mailed Aug. 1, 2017.

Non-Final Office Action for U.S. Appl. No. 14/952,591 mailed Mar. 20, 2020.

Non-Final Office Action for U.S. Appl. No. 14/952,591 mailed Mar. 21, 2019.

Non-Final Office Action for U.S. Appl. No. 14/952,591 mailed Sep. 28, 2018.

Non-Final Office Action for U.S. Appl. No. 15/171,968 mailed May 11, 2020.

Non-Final Office Action for U.S. Appl. No. 15/171,968 mailed Jun. 12, 2018.

Non-Final Office Action for U.S. Appl. No. 15/171,968 mailed Aug. 20, 2019.

Non-Final Office Action for U.S. Appl. No. 15/221,106 mailed Jun. 5, 2018.

Non-Final Office Action for U.S. Appl. No. 15/238,427 mailed Aug. 8, 2018.

Non-Final Office Action for U.S. Appl. No. 15/260,103 mailed Sep. 26, 2018.

Non-Final Office Action for U.S. Appl. No. 15/611,587 mailed Dec. 29, 2017.

Non-Final Office Action for U.S. Appl. No. 15/611,587 mailed Jul. 13, 2018.

Non-Final Office Action for U.S. Appl. No. 15/612,325 mailed Mar. 19, 2020.

Non-Final Office Action for U.S. Appl. No. 16/899,956 mailed Oct. 16, 2020.

Non-Final Office Action for U.S. Appl. No. 29/624,661 mailed Jul. 18, 2019.

Non-Final Office Action for U.S. Appl. No. 29/694,002 mailed Jun. 24, 2020.

Notice of Allowance for U.S. Appl. No. 15/221,106 mailed May 1, 2019.

Notice of Allowance for U.S. Appl. No. 15/238,427 mailed May 23, 2019.

Notice of Allowance for U.S. Appl. No. 15/260,103 mailed Jun. 7, 2019.

Notice of Allowance for U.S. Appl. No. 15/611,587 mailed Dec. 21, 2018.

Notice of Allowance for U.S. Appl. No. 29/624,661 mailed Jul. 10, 2020.

Notice of Allowance for U.S. Appl. No. 29/624,661 mailed May 14, 2020.

Notice of Allowance for U.S. Appl. No. 29/624,661 mailed Sep. 29, 2020.

Notice of Allowance for U.S. Appl. No. 29/694,002 mailed Oct. 16, 2020.

U.S. Appl. No. 15/171,968, filed Jun. 2, 2016.

U.S. Appl. No. 15/221,106, filed Jul. 27, 2016.

U.S. Appl. No. 15/260,103, filed Sep. 8, 2016.

U.S. Appl. No. 15/611,587, filed Jun. 1, 2017.

U.S. Appl. No. 16/369,676, filed Mar. 29, 2019.

U.S. Appl. No. 16/433,773, filed Jun. 6, 2019.

U.S. Appl. No. 16/449,039, filed Jun. 21, 2019.

U.S. Appl. No. 16/452,145, filed Jun. 25, 2019.

U.S. Appl. No. 16/452,258, filed Jun. 25, 2019.

U.S. Appl. No. 16/478,180, filed Jul. 16, 2019.

U.S. Appl. No. 16/904,868, filed Jun. 18, 2020.

U.S. Appl. No. 16/905,400, filed Jun. 18, 2020.

U.S. Appl. No. 29/741,751, filed Jul. 15, 2020.

U.S. Appl. No. 62/452,437, filed Jan. 31, 2017.

U.S. Appl. No. 62/665,297, filed May 1, 2018.

U.S. Appl. No. 62/665,302, filed May 1, 2018.

U.S. Appl. No. 62/665,317, filed May 1, 2018.

U.S. Appl. No. 62/665,321, filed May 1, 2018.

U.S. Appl. No. 62/665,331, filed May 1, 2018.

U.S. Appl. No. 62/665,335, filed May 1, 2018.

U.S. Appl. No. 62/853,889, filed May 29, 2019.

U.S. Appl. No. 62/873,045, filed Jul. 11, 2019.

U.S. Appl. No. 62/873,048, filed Jul. 11, 2019.

U.S. Appl. No. 62/994,912, filed Mar. 26, 2020.

U.S. Appl. No. 63/011,445, filed Apr. 17, 2020.

U.S. Appl. No. 63/011,487, filed Apr. 17, 2020.

U.S. Appl. No. 63/011,571, filed Apr. 17, 2020.

U.S. Appl. No. 63/011,657, filed Apr. 17, 2020.

U.S. Appl. No. 63/011,760, filed Apr. 17, 2020.

U.S. Appl. No. 63/012,347, filed Apr. 20, 2020.

U.S. Appl. No. 63/012,384, filed Apr. 20, 2020.

(56)                    References Cited

OTHER PUBLICATIONS

U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/071,438, filed Aug. 28, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/094,464, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
Defendant and Counterclaim Plaintiff Sage Products, LLC's Answer, Defenses, and Counterclaims to Plaintiff's Amended Complaint, Nov. 1, 2019.
Hollister Female Urinary and Pouch and Male Urinary Pouch Brochure, 2011, 1 page.
3 Devices Take Top Honors in Dare-To-Dream Medtech Design Contest, 2014, 1 page.
Omni Medical AMXD Starter Kit Brochure, 15 pages.
Sage's Initial Invalidity Contentions Regarding U.S. Pat. Nos. 8,287,508; 10,226,375; and 10,390,989, May 29, 2020, 193 pages.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Excerpts from the 508 (U.S. Pat. No. 8,278,508) Patent's Prosecution History, 2020, 99 pages.
PureWick's Response to Interrogatory No. 9 in *PureWick, LLC* v. *Sage Products, LLC*, Case No. 19-1508-MN, 2020, 6 pages.
Corrected Certificate of Service, Case No. IPR2020-01426, U.S. Pat. No. 8,287,508, 2020, 2 pages.
"AMXDX—Advanced Mission Extender Device Brochure", Omni Medical, Omni Brochure—http://www.omnimedicalsys.com/uploads/AMXDFixedWing.pdf, 2 pages.
"How Period Panties Work", www.shethinx.com/pages/thinx-itworks, 2020, 10 pages.
"In Flight Bladder Relief", Omni Medical, Omni Presentation https://www.omnimedicalsys.com/uploads/AMXDmax_HSD.pdf, 14 pages.
"Male Urinary Pouch External Collection Device", http://www.hollister.com/en/products/Continence-Care-Products/Urine-Collectors/Urine-Collection-Accessories/Male-Urinary-Pouch-External-Collection-Device, last accessed Feb. 8, 2018.
"Plaintiff's Identification of Claim Terms and Proposed Constructions", Case No. 19-1508-MN, 3 pages.
"Plaintiff's Opening Claim Construction Brief", Case No. 19-1508-MN, 2020, 26 pages.
"Research and Development Work Relating to Assistive Technology Jun. 2005", British Department of Health, 2006, 40 pages.
"Sage's Preliminary Identification of Claim Elements and Proposed Constructions for U.S. Pat. Nos. 8,287,508, 10,226,376, 10,390,989 and 10,376,407", Case No. 19-1508-MN, 7 pages.
"Step by Step How Ur24 WorksHome", http://medicalpatentur24.com, last accessed Dec. 6, 2017, Aug. 30, 2017, 4 pages.
"Underwear that absorbs your period", Thinx!, https://www.shethinx.com/pages/thinx-it-works last accessed Jun. 24, 2020, 7 pages.
Hollister, "Retracted Penis Pouch by Hollister", Vitality Medical.com, https://www.vitalitymedical.com/hollister-retracted-penis-pouch.html last accessed Jun. 24, 2020, 6 pages.

Macaulay, et al., "A Noninvasive Continence Management System: Development and Evaluation of a Novel Toileting Device for Women", The Wound, Ostomy and Continence Nurses Society, vol. 34 No. 6, 2007, pp. 641-648.
Newman, "Declaration of Diane K. Newman Curriculum Vitae", Petition for Interparties Review, 2020, pp. 1-199.
Newman, et al., "The Urinary Incontinence Sourcebook", Petition for Interparties Review, 1997, 23 pages.
Parmar, "10 Finalists Chosen for Dare-to-Dream Medtech Design Challenge (PureWick)," Design Services, Nov. 10, 2014 (3 pages).
Purewick, "Incontinence Relief for Women" Presentation, (7 pages), Sep. 23, 2015.
Pytlik, "Super Absorbent Polymers," University of Buffalo http://www.courses.sens.buffalo.edu/ce435/Diapers/Diapers.html, accessed on Feb. 17, 2017.
Sachtman, "New Relief for Pilots? It Depends", Wired, https://www.wired.com/2008/05/pilot-relief/, 2008, 2 pages.
Advisory Action for U.S. Appl. No. 16/905,400 mailed Jun. 9, 2021.
Corrected Notice of Allowability for U.S. Appl. No. 15/612,325 mailed Mar. 17, 2021.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Issue Notification for U.S. Appl. No. 15/171,968 mailed Mar. 3, 2021.
Issue Notification for U.S. Appl. No. 15/612,325 mailed Mar. 24, 2021.
Notice of Allowance for U.S. Appl. No. 14/952,591 mailed Apr. 5, 2021.
Notice of Allowance for U.S. Appl. No. 15/171,968 mailed Feb. 16, 2021.
Notice of Allowance for U.S. Appl. No. 15/612,325 mailed Feb. 19, 2021.
Notice of Allowance for U.S. Appl. No. 29/624,661 mailed Apr. 28, 2021.
Notice of Allowance for U.S. Appl. No. 29/694,002 mailed Apr. 29, 2021.
Notice of Allowance for U.S. Appl. No. 29/694,002 mailed Jan. 29, 2021.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 17/179,116, filed Feb. 18, 2021.
U.S. Appl. No. 17/330,657 mailed May 26, 2021.
U.S. Appl. No. 63/148,723, filed Feb. 12, 2021.
Memorandum Order, Feb. 2021, 14 pgs.
Boehringer CareDry System—Second Generation for Non-Invasive Urinary Management for Females, Mar. 2021, 3 pgs.
Decision Granting Institution of Inter Partes Review for U.S. Pat. No. 8,287,508, Case No. 2020-01426, Feb. 17, 2021, 39 pages.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/904,868 mailed Jun. 15, 2022.
Advisory Action for U.S. Appl. No. 16/905,400 mailed Feb. 16, 2022.
Corrected Notice of Allowability for U.S. Appl. No. 17/330,657 mailed Dec. 9, 2021.
Final Office Action for U.S. Appl. No. 16/245,726 mailed Nov. 25, 2022.
Final Office Action for U.S. Appl. No. 16/369,676 mailed Dec. 5, 2022.

(56)                    References Cited

OTHER PUBLICATIONS

Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/904,868 mailed Mar. 10, 2022.
Final Office Action for U.S. Appl. No. 16/905,400 mailed Dec. 9, 2021.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.
International Search Report and Written Opinion from International Application No. PCT/US2020/055680 mailed Dec. 15, 2020.
International Search Report and Written Opinion from International Application No. PCT/US2020/057562 mailed Jan. 27, 2021.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/026607 mailed Jul. 29, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.

International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
International Search Report and Written Opinion from International Application No. PCT/US2021/039866 mailed Oct. 7, 2021.
International Search Report and Written Opinion from International Application No. PCT/US2021/043893 mailed Nov. 22, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.

(56)      References Cited

OTHER PUBLICATIONS

International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.
International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039714 mailed Nov. 22, 2022.
International Search Report and Written Opinion from International Application No. PCT/US2022/042719 mailed Dec. 5, 2022.
International Search Report and Written Opinion from International Application No. PCT/US2022/044107 mailed Dec. 23, 2022.
Issue Notification for U.S. Appl. No. 14/952,591 mailed Jul. 28, 2021.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Issue Notification for U.S. Appl. No. 29/624,661 mailed Aug. 4, 2021.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 21, 2022.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Dec. 20, 2022.
Non-Final Office Action for U.S. Appl. No. 16/478,180 mailed Oct. 22, 2021.
Non-Final Office Action for U.S. Appl. No. 16/899,956 mailed Sep. 2, 2021.
Non-Final Office Action for U.S. Appl. No. 16/904,868 mailed Oct. 5, 2021.
Non-Final Office Action for U.S. Appl. No. 16/905,400 mailed Apr. 27, 2022.
Non-Final Office Action for U.S. Appl. No. 16/905,400 mailed Jul. 22, 2021.
Non-Final Office Action for U.S. Appl. No. 17/051,550 mailed Dec. 15, 2022.
Non-Final Office Action for U.S. Appl. No. 17/330,657 mailed Aug. 11, 2021.
Non-Final Office Action for U.S. Appl. No. 17/451,345 mailed Dec. 7, 2022.

Non-Final Office Action for U.S. Appl. No. 17/662,700 mailed Jul. 22, 2022.
Non-Final Office Action for U.S. Appl. No. 29/741,751 mailed Jan. 18, 2022.
Notice of Allowance for U.S. Appl. No. 14/952,591 mailed Jul. 8, 2021.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/088,272 mailed Aug. 5, 2021.
Notice of Allowance for U.S. Appl. No. 17/088,272 mailed Mar. 4, 2022.
Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Oct. 6, 2022.
Notice of Allowance for U.S. Appl. No. 29/741,751 mailed Jun. 9, 2022.
Restriction Requirement for U.S. Appl. No. 16/433,773 mailed Dec. 7, 2021.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/384,196, filed Dec. 19, 2016.
U.S. Appl. No. 15/612,325, filed Jun. 2, 2017.
U.S. Appl. No. 16/245,726, filed Jan. 11, 2019.
U.S. Appl. No. 17/378,015, filed Jul. 16, 2021.
U.S. Appl. No. 17/394,055, filed Aug. 4, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,260, filed Nov. 2, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/645,821, filed Dec. 23, 2021.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/654,156, filed Mar. 9, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.

(56)               References Cited

OTHER PUBLICATIONS

U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.
U.S. Appl. No. 17/999,648, filed Nov. 22, 2022.
U.S. Appl. No. 18/003,029, filed Dec. 22, 2022.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/485,578, filed Apr. 14, 2017.
U.S. Appl. No. 62/853,279, filed May 28, 2019.
U.S. Appl. No. 62/864,656, filed Jun. 21, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/067,542, filed Aug. 19, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/088,539, filed Oct. 7, 2020.
U.S. Appl. No. 63/094,498, filed Oct. 21, 2020.
U.S. Appl. No. 63/094,646, filed Oct. 21, 2020.
U.S. Appl. No. 63/109,066, filed Nov. 3, 2020.
U.S. Appl. No. 63/109,084, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,450, filed Jan. 6, 2021.
U.S. Appl. No. 63/134,631, filed Jan. 7, 2021.
U.S. Appl. No. 63/134,754, filed Jan. 7, 2021.
U.S. Appl. No. 63/138,878, filed Jan. 19, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.

U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/191,558, filed May 21, 2021.
U.S. Appl. No. 63/192,274, filed May 24, 2021.
U.S. Appl. No. 63/192,289, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.
U.S. Appl. No. 63/208,262, filed Jun. 8, 2021.
U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/230,897, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,328, filed Sep. 7, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
U.S. Appl. No. 63/299,208, filed Jan. 13, 2022.
"External Urine Management for Female Anatomy", https://www.stryker.com/us/en/sage/products/sage-primafit.html, Jul. 2020, 4 pages.
"Rising Warrior Insulated Gallon Jug Cover", https://www.amazon.com/Rising-Warrior-Insulated-Sleeve, 2021, 2 pages.
"Urine Bag Cover-Catheter Bag Cover 2000 ml Volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali , "Sustainability Assessment: Seventh Generation Diapers versus gDiapers", The University of Vermont, Dec. 6, 2011, pp. 1-31.
Autumn , et al., "Frictional adhesion: a new angle on gecko attachment", The Journal of Experimental Biology, 2006, pp. 3569-3579.
Cañas , et al., "Effect of nano- and micro-roughness on adhesion of bioinspired micropatterned surfaces", Acta Biomaterialia 8, 2012, pp. 282-288.
Chaudhary , et al., "Bioinspired dry adhesive: Poly(dimethylsiloxane) grafted with poly(2-ethylhexyl acrylate) brushes", European Polymer Journal, 2015, pp. 432-440.
Dai , et al., "Non-sticky and Non-slippery Biomimetic Patterned Surfaces", Journal of Bionic Engineering, Mar. 2020, pp. 326-334.
Espinoza-Ramirez , "Nanobiodiversity and Biomimetic Adhesives Development: From Nature to Production and Application", Journal of Biomaterials and Nanobiotechnology, pp. 78-101, 2019.
Hwang , et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong , et al., "A nontransferring dry adhesive with hierarchical polymer nanohairs", PNAS, Apr. 7, 2009, pp. 5639-5644.
Jeong , et al., "Nanohairs and nanotubes: Efficient structural elements for gecko-inspired artificial dry adhesives", Science Direct, 2009, pp. 335-346.
Karp , et al., "Dry solution to a sticky problem", Nature., 2011, pp. 42-43.

(56) References Cited

OTHER PUBLICATIONS

Lee, et al., "Continuous Fabrication of Wide-Tip Microstructures for Bio-Inspired Dry Adhesives via Tip Inking Process", Journal of Chemistry, Jan. 2, 2019, pp. 1-5.

Parness , et al., "A microfabricated wedge-shaped adhesive array displaying gecko-like dynamic adhesion, directionality", J.R. Soc. Interface, 2009, pp. 1223-1232.

Tsipenyuk , et al., "Use of biomimetic hexagonal surface texture in friction against lubricated skin", Journal of The Royal Society—Interface, 2014, pp. 1-6.

Advisory Action for U.S. Appl. No. 16/245,726 mailed Apr. 19, 2023.

Advisory Action for U.S. Appl. No. 16/369,676 mailed Mar. 24, 2023.

Advisory Action for U.S. Appl. No. 16/433,773 mailed Feb. 15, 2023.

Advisory Action for U.S. Appl. No. 17/662,700 mailed Jan. 30, 2023.

Final Office Action for U.S. Appl. No. 16/478,180 mailed May 31, 2023.

Final Office Action for U.S. Appl. No. 17/051,550 mailed May 23, 2023.

Final Office Action for U.S. Appl. No. 17/451,345 mailed May 3, 2023.

International Search Report and Written Opinion from International Application No. PCT/US2022/039018 mailed Jan. 10, 2023.

International Search Report and Written Opinion from International Application No. PCT/US2022/039022 mailed Jan. 10, 2023.

International Search Report and Written Opinion from International Application No. PCT/US2022/039711 mailed Jan. 12, 2023.

International Search Report and Written Opinion from International Application No. PCT/US2022/041085 mailed Mar. 16, 2023.

International Search Report and Written Opinion from International Application No. PCT/US2022/041688 mailed Nov. 21, 2022.

International Search Report and Written Opinion from International Application No. PCT/US2022/042725 mailed Dec. 19, 2022.

International Search Report and Written Opinion from International Application No. PCT/US2022/044212 mailed Jan. 20, 2023.

International Search Report and Written Opinion from International Application No. PCT/US2022/044243 mailed Feb. 24, 2023.

Issue Notification for U.S. Appl. No. 16/899,956 mailed Mar. 29, 2023.

Non-Final Office Action for U.S. Appl. No. 16/433,773 mailed Apr. 11, 2023.

Non-Final Office Action for U.S. Appl. No. 16/449,039 mailed Apr. 27, 2023.

Non-Final Office Action for U.S. Appl. No. 16/452,145 mailed Mar. 28, 2023.

Non-Final Office Action for U.S. Appl. No. 16/452,258 mailed Apr. 26, 2023.

Non-Final Office Action for U.S. Appl. No. 16/904,868 mailed Mar. 15, 2023.

Non-Final Office Action for U.S. Appl. No. 17/051,585 mailed Mar. 29, 2023.

Non-Final Office Action for U.S. Appl. No. 17/179,116 mailed Mar. 24, 2023.

Non-Final Office Action for U.S. Appl. No. 17/444,792 mailed Feb. 10, 2023.

Non-Final Office Action for U.S. Appl. No. 17/446,256 mailed Apr. 13, 2023.

Non-Final Office Action for U.S. Appl. No. 17/448,811 mailed Mar. 1, 2023.

Non-Final Office Action for U.S. Appl. No. 17/450,864 mailed May 10, 2023.

Non-Final Office Action for U.S. Appl. No. 17/451,354 mailed May 3, 2023.

Non-Final Office Action for U.S. Appl. No. 17/453,260 mailed Mar. 14, 2023.

Non-Final Office Action for U.S. Appl. No. 17/501,591 mailed Apr. 25, 2023.

Non-Final Office Action for U.S. Appl. No. 17/653,137 mailed Apr. 7, 2023.

Non-Final Office Action for U.S. Appl. No. 17/655,464 mailed Mar. 14, 2023.

Notice of Allowance for U.S. Appl. No. 17/461,036 mailed Feb. 22, 2023.

Notice of Allowance for U.S. Appl. No. 17/662,700 mailed Mar. 28, 2023.

Notice of Allowance for U.S. Appl. No. 17/663,046 mailed Jan. 30, 2023.

Restriction Requirement for U.S. Appl. No. 17/326,980 mailed Mar. 20, 2023.

Restriction Requirement for U.S. Appl. No. 17/446,256 mailed Jan. 23, 2023.

Restriction Requirement for U.S. Appl. No. 17/646,771 mailed Apr. 6, 2023.

Text Messages to Lorena Eckert Re Prototype PureWick Holder dated Apr. 16, 2022.

U.S. Appl. No. 18/006,807, filed Jan. 25, 2023.

U.S. Appl. No. 18/007,105, filed Jan. 27, 2023.

U.S. Appl. No. 18/041,109, filed Feb. 9, 2023.

U.S. Appl. No. 18/042,842, filed Feb. 24, 2023.

U.S. Appl. No. 18/043,618, filed Mar. 1, 2023.

U.S. Appl. No. 18/115,444, filed Feb. 28, 2023.

U.S. Appl. No. 18/134,857, filed Apr. 14, 2023.

U.S. Appl. No. 18/140,163, filed Apr. 27, 2023.

U.S. Appl. No. 18/140,751, filed Apr. 28, 2023.

U.S. Appl. No. 18/164,800, filed Feb. 6, 2023.

U.S. Appl. No. 18/198,464, filed May 17, 2023.

U.S. Appl. No. 18/246,121, filed Mar. 21, 2023.

U.S. Appl. No. 18/247,986, filed Apr. 5, 2023.

U.S. Appl. No. 18/299,788, filed Apr. 13, 2023.

U.S. Appl. No. 63/308,190, filed Feb. 9, 2022.

*PureWick Corporation* v. *Sage Products, LLC* Transcripts vol. 5, Apr. 1, 2022, 72 pages.

*PureWick Corporation* v. *Sage Products, LLC* Transcripts vol. 1, Mar. 28, 2022, 99 pages.

*PureWick Corporation* v. *Sage Products, LLC* Transcripts vol. 2, Mar. 29, 2022, 106 pages.

*PureWick Corporation* v. *Sage Products, LLC* Transcripts vol. 3, Mar. 30, 2022, 115 pages.

*PureWick Corporation* v. *Sage Products, LLC* Transcripts vol. 4, Mar. 31, 2022, 117 pages.

"AMXD Control Starter Kit", Omni Medical Systems, Inc., 1 page.

"AMXDmax Advanced Mission Extender Device User & Maintenance Guide", Omni Medical, Jan. 11, 2010, 10 pages.

"AMXDmax Development History 2002-2014", Omni Medical Systems, Inc., 2 pages.

"Combat Force Multiplier in Flight Bladder Relief Cockpit Essential Equipment Brochure", Omni Medical, 20 pages.

"GSA Price List", Omni Medical, Apr. 2011, 2 pages.

"How is Polypropylene Fiber Made", https:www.yarnsandfibers.com/textile-resources/synthetic-fibers/polypropylene-fiber/polypropylene-fiber-production-raw-materials/how-is-polypropylene-fiber-made/ last accessed 2020, Oct. 7, 2020, 3 pages.

"Letter to Mark Harvie of Omni Measurement Systems", Department of Veterans Affairs, Nov. 1, 2007, 11 pages.

"Revised AMXDmax Advanced Mission Extender Device User & Maintenance Guide", Omni Medical Systems, Oct. 8, 2019, 52 pages.

Pieper , et al., "An external urine-collection device for women: A clinical trial", Journal of ER Nursing, vol. 20, No. 2, Mar./Apr. 1993, pp. 51-55.

Vinas , "A Solution For An Awkward—But Serious—Subject", http://www.aero-news.net/index.cfm?do=main.textpost&id=69ae2bb1-838b-4098-a7b5-7flbb2505688 last accessed Feb. 8, 2021, 3 pages.

Advisory Action for U.S. Appl. No. 16/478,180 mailed Sep. 7, 2023.

Advisory Action for U.S. Appl. No. 17/051,550 mailed Sep. 8, 2023.

Advisory Action for U.S. Appl. No. 17/051,585 mailed Oct. 17, 2023.

Advisory Action for U.S. Appl. No. 17/444,792 mailed Aug. 25, 2023.

(56) References Cited

OTHER PUBLICATIONS

Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/653,137 mailed Dec. 1, 2023.
Advisory Action for U.S. Appl. No. 17/655,464 mailed Dec. 13, 2023.
Corrected Notice of Allowance for U.S. Appl. No. 16/369,676 mailed Dec. 7, 2023.
Final Office Action for U.S. Appl. No. 16/369,676 mailed Aug. 31, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/904,868 mailed Nov. 2, 2023.
Final Office Action for U.S. Appl. No. 17/051,585 mailed Jul. 27, 2023.
Final Office Action for U.S. Appl. No. 17/179,116 mailed Oct. 31, 2023.
Final Office Action for U.S. Appl. No. 17/444,792 mailed Jun. 15, 2023.
Final Office Action for U.S. Appl. No. 17/446,256 mailed Sep. 19, 2023.
Final Office Action for U.S. Appl. No. 17/448,811 mailed Aug. 3, 2023.
Final Office Action for U.S. Appl. No. 17/451,354 mailed Oct. 30, 2023.
Final Office Action for U.S. Appl. No. 17/453,260 mailed Oct. 5, 2023.
Final Office Action for U.S. Appl. No. 17/501,591 mailed Nov. 14, 2023.
Final Office Action for U.S. Appl. No. 17/653,137 mailed Sep. 21, 2023.
Final Office Action for U.S. Appl. No. 17/655,464 mailed Sep. 1, 2023.
Final Office Action for U.S. Appl. No. 17/661,090 mailed Dec. 11, 2023.
Final Office Action for U.S. Appl. No. 18/164,800 mailed Dec. 6, 2023.
International Search Report and Written Opinion from International Application No. PCT/US2022/043818 mailed Mar. 24, 2023.
International Search Report and Written Opinion from International Application No. PCT/US2022/044208 mailed May 8, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
International Search Report and Written Opinion from International Application No. PCT/US2023/018474 mailed Sep. 11, 2023.
Issue Notification for U.S. Appl. No. 16/245,726 mailed Oct. 18, 2023.
Issue Notification for U.S. Appl. No. 17/461,036 mailed Oct. 11, 2023.
Non-Final Office Action for U.S. Appl. No. 16/452,145 mailed Nov. 2, 2023.
Non-Final Office Action for U.S. Appl. No. 16/478,180 mailed Nov. 7, 2023.
Non-Final Office Action for U.S. Appl. No. 17/051,550 mailed Oct. 24, 2023.
Non-Final Office Action for U.S. Appl. No. 17/326,980 mailed Jul. 11, 2023.

Non-Final Office Action for U.S. Appl. No. 17/446,654 mailed Sep. 8, 2023.
Non-Final Office Action for U.S. Appl. No. 17/453,560 mailed Oct. 16, 2023.
Non-Final Office Action for U.S. Appl. No. 17/645,821 mailed Oct. 25, 2023.
Non-Final Office Action for U.S. Appl. No. 17/646,771 mailed Jul. 5, 2023.
Non-Final Office Action for U.S. Appl. No. 17/657,474 mailed Sep. 12, 2023.
Non-Final Office Action for U.S. Appl. No. 17/661,090 mailed Jul. 6, 2023.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 17/808,354 mailed Nov. 28, 2023.
Non-Final Office Action for U.S. Appl. No. 18/139,523 mailed Aug. 17, 2023.
Non-Final Office Action for U.S. Appl. No. 18/140,163 mailed Nov. 9, 2023.
Non-Final Office Action for U.S. Appl. No. 18/140,751 mailed Sep. 14, 2023.
Non-Final Office Action for U.S. Appl. No. 18/198,464 mailed Dec. 7, 2023.
Notice of Allowance for U.S. Appl. No. 16/245,726 mailed Jul. 6, 2023.
Notice of Allowance for U.S. Appl. No. 16/369,676 mailed Nov. 14, 2023.
Notice of Allowance for U.S. Appl. No. 17/051,554 mailed Jul. 6, 2023.
Notice of Allowance for U.S. Appl. No. 17/051,554 mailed Oct. 18, 2023.
Notice of Allowance for U.S. Appl. No. 17/461,036 mailed Jun. 30, 2023.
Notice of Allowance for U.S. Appl. No. 17/662,700 mailed Jul. 28, 2023.
Notice of Allowance for U.S. Appl. No. 17/662,700 mailed Nov. 15, 2023.
Notice of Allowance for U.S. Appl. No. 18/299,788 mailed Jul. 24, 2023.
Notice of Allowance for U.S. Appl. No. 18/299,788 mailed Nov. 6, 2023.
Restriction Requirement for U.S. Appl. No. 17/051,600 mailed Sep. 21, 2023.
Restriction Requirement for U.S. Appl. No. 17/645,821 mailed Jul. 12, 2023.
Restriction Requirement for U.S. Appl. No. 17/657,474 mailed Jun. 30, 2023.
Restriction Requirement for U.S. Appl. No. 18/134,857 mailed Oct. 23, 2023.
U.S. Appl. No. 17/451,719, filed Oct. 19, 2021.
U.S. Appl. No. 17/664,487, filed May 23, 2022.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/335,579, filed Jun. 15, 2023.
U.S. Appl. No. 18/373,424, filed Sep. 27, 2023.
U.S. Appl. No. 18/376,274, filed Oct. 3, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 18/553,625, filed Oct. 2, 2023.
U.S. Appl. No. 18/556,945, filed Oct. 24, 2023.
U.S. Appl. No. 18/558,502, filed Nov. 1, 2023.
U.S. Appl. No. 18/562,626, filed Nov. 20, 2023.
U.S. Appl. No. 18/563,672, filed Nov. 22, 2023.
U.S. Appl. No. 18/569,711, filed Dec. 13, 2023.

(56)        References Cited

OTHER PUBLICATIONS

U.S. Appl. No. 18/569,778, filed Dec. 13, 2023.
U.S. Appl. No. 63/150,640, filed Feb. 18, 2021.
U.S. Appl. No. 63/596,012, filed Nov. 3, 2023.
U.S. Appl. No. 63/608,553, filed Dec. 11, 2023.
Merriam-Webster Dictionary, "Embed Definition & Meaning", https://
www.merriam-webster.com/dictionary/embed last accessed Aug. 3,
2023, 2003.

* cited by examiner

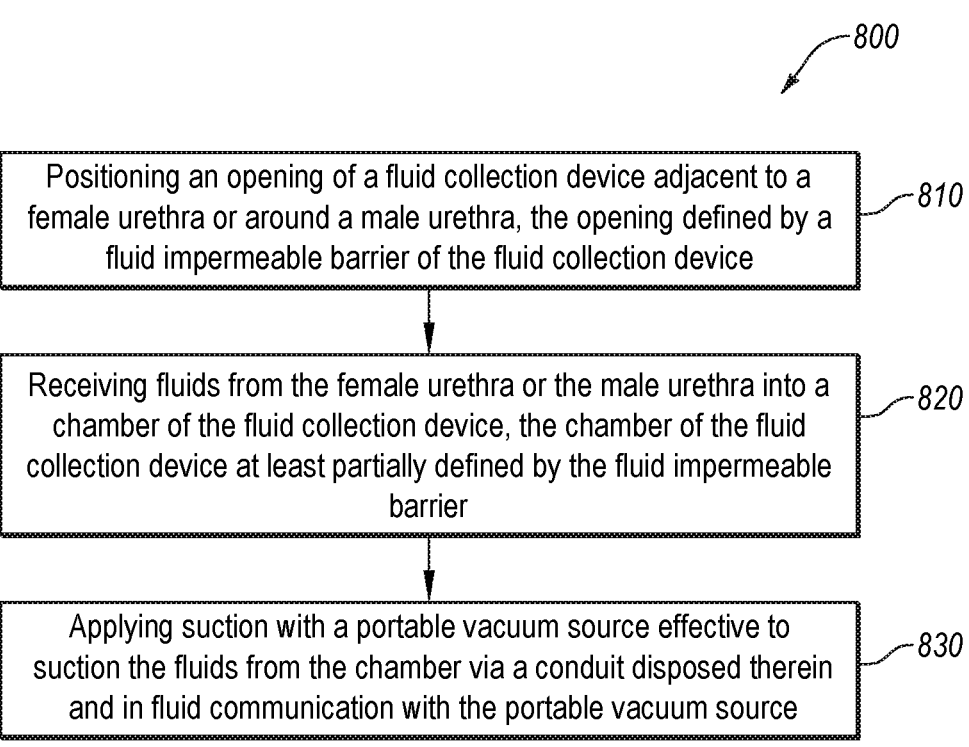

_800_

_810_ | Positioning an opening of a fluid collection device adjacent to a female urethra or around a male urethra, the opening defined by a fluid impermeable barrier of the fluid collection device _820_ | Receiving fluids from the female urethra or the male urethra into a chamber of the fluid collection device, the chamber of the fluid collection device at least partially defined by the fluid impermeable barrier _830_ | Applying suction with a portable vacuum source effective to suction the fluids from the chamber via a conduit disposed therein and in fluid communication with the portable vacuum source

_FIG. 8_

1

FLUID COLLECTION DEVICES, SYSTEMS, AND METHODS

CROSS-REFERENCE TO RELATED APPLICATIONS

This application is U.S. Nationalization of PCT International Application No. PCT/US2019/029608 filed on 29 Apr. 2019, which claims priority to U.S. Provisional Application No. 62/665,302 filed on 1 May 2018, the disclosure of each of which is incorporated herein in its entirety by this reference.

BACKGROUND

An individual may have limited or impaired mobility such that typical urination processes are challenging or impossible. For example, the individual may have surgery or a disability that impairs mobility. In another example, the individual may have restricted travel conditions such as those experience by pilots, drivers, and workers in hazardous areas. Additionally, fluid collection from the individual may be needed for monitoring purposes or clinical testing.

Bed pans and urinary catheters, such as a Foley catheter, can be used to address some of these circumstances. However, bed pans and urinary catheters have several problems associated therewith. For example, bed pans can be prone to discomfort, spills, and other hygiene issues. Urinary catheters be can be uncomfortable, painful, and can cause urinary tract infections.

Thus, users and manufacturers of fluid collection devices continue to seek new and improved devices, systems, and methods to collect urine.

SUMMARY

Embodiments disclosed herein are related to devices, systems, and methods of using fluid collection devices. In an embodiment, a fluid collection system is disclosed. The fluid collection system includes a fluid storage container configured to hold a fluid. The fluid collection system includes a fluid collection device in fluid communication with the fluid storage container. The fluid collection device includes a fluid impermeable barrier at least partially defining a chamber, the fluid impermeable barrier also defining an opening extending therethrough, the opening configured to be positioned adjacent to a female urethra or have a male urethra positioned therethrough. The fluid collection device includes a conduit including an inlet and an outlet, the inlet being positioned within the fluid collection device and the outlet is configured to be in fluid communication with the fluid storage container. The fluid collection system includes a portable vacuum source in fluid communication with one or more of the fluid storage container or the fluid collection device, the portable vacuum source configured to draw fluid from the fluid collection device.

In an embodiment, a method to collect fluid is disclosed. The method includes positioning an opening of a fluid collection device adjacent to a female urethra or around a male urethra, the opening defined by a fluid impermeable barrier of the fluid collection device. The method includes receiving fluid from the female urethra or the male urethra into a chamber of the fluid collection device, the chamber of the fluid collection device at least partially defined by the fluid impermeable barrier. The method includes applying suction with a portable vacuum source effective to suction the fluid from the chamber via a conduit disposed therein and in fluid communication with the portable suction device.

In an embodiment, a fluid collection system is disclosed. The fluid collection system includes a fluid storage container configured to hold a fluid. The fluid collection system includes a fluid collection device in fluid communication with the fluid storage container. The fluid collection device includes a fluid impermeable barrier at least partially defining a chamber, the fluid impermeable barrier also defining an opening configured to be positioned adjacent to a female urethra or have a male urethra positioned therethrough. The fluid collection device includes a conduit including an inlet and an outlet, the outlet being in fluid communication with the fluid storage container and the inlet being positioned in a portion of the chamber selected to be at a gravimetrically low point of the fluid collection device when worn by a user. The fluid collection system includes a portable vacuum source in fluid communication with one or more of the fluid storage container or the fluid collection device via the conduit, the portable vacuum source configured to draw fluid from the fluid collection device via the conduit.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

FIG. 8 is a flow diagram of a method to collect fluid, according to an embodiment.

DETAILED DESCRIPTION

Figure 1:
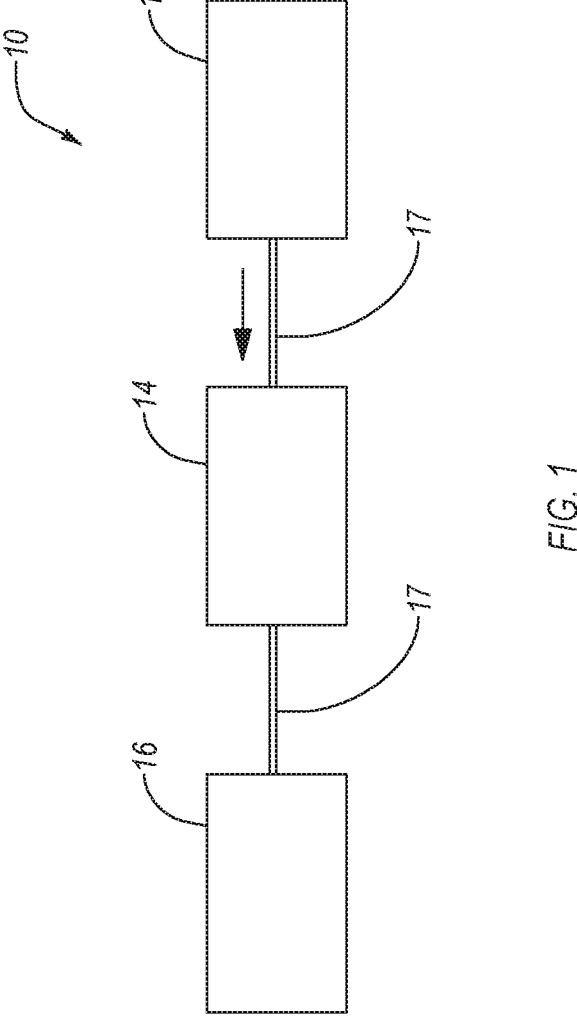
FIG. 1 is a block diagram of a system for fluid collection, according to an embodiment.

Embodiments disclosed herein are related to devices, systems, and methods of using fluid collection devices and systems. The devices, systems, and methods of using fluid collection devices and systems include a portable vacuum source to remove urine from the fluid collection device. The portable vacuum source may allow for portable usage of the systems and methods herein such as in non-hospital environments.

In an example, a fluid collection device includes a fluid impermeable barrier that at least partially defines a chamber. The fluid impermeable barrier also defines an opening extending therethrough that is configured to be positioned adjacent to a female urethra or have a male urethra positioned therethrough. The fluid collection device also includes a tube having a channel extending between an inlet and outlet thereof. The inlet is configured to be coupled to a suction source and the outlet is configured to be in fluid communication with (e.g., fluidly coupled to) a fluid storage (vessel or container). The outlet is positioned downstream from the inlet. The channel also defines at least one aperture therein that fluidly couples an interior of the channel to the rest of the chamber.

The fluid collection devices disclosed herein are configured to collect fluid(s) from an individual. The fluid collected by the fluid collection devices can include urine. The fluid(s) collected by the fluid collection devices can also include at least one of vaginal discharge, penile discharge, reproductive fluids, blood, sweat, or other bodily fluids.

The fluid collection devices disclosed herein are configured to be used in fluid collection systems. The fluid collection systems disclosed herein include a gas source. Systems that include a gas source can, in some examples, resolve several problems associated with systems that include a vacuum source. For example, a system that includes a vacuum source draws fluid(s) towards the vacuum source and deposits most of the fluid(s) in a fluid storage container before the fluid(s) can reach the vacuum source. However, a small quantity of fluid(s) (e.g., vapor from the fluid(s)) can still reach the vacuum source, which can contaminate and/or damage (e.g., rust) the vacuum source. Additionally, a large quantity of the fluid(s) can reach the vacuum source when the fluid storage container is substantially full. However, a system that includes a gas source (e.g., compressed air) moves the fluid(s) away from the gas source, thereby preventing contamination and/or damage though splashing or spray of the fluid(s) may be a problem with a gas. For example, a gas source may be used to create a vacuum by flowing a gas past a connected end of the conduit at a perpendicular or oblique angle to the conduit to create a vacuum in the conduit. The fluids are pulled up the conduit and into the gas flow in the direction of the gas flow, which is away from the gas source. In another example, systems that include a vacuum source cannot be used in environments that do not include an available vacuum source (e.g., a patient's room does not include a vacuum source or the vacuum source is being used). As such, systems that include a gas source can be used in environments that do not include an available vacuum source. A liquid source such as water can be used to create and implement a vacuum in the same way as the gas source. The vacuum source or gas source can be utilized with any of the devices or systems disclosed herein to remove a fluid therefrom.

FIG. 1 is a block diagram of a system 10 for fluid collection, according to an embodiment. The system 10 includes a fluid collection device 12, a fluid storage container 14, and a portable vacuum source 16. The fluid collection device 12, the fluid storage container 14, and the portable vacuum source 16 may be fluidly coupled to (e.g., in fluid communication with) each other via one or more conduits 17. For example, fluid collection device 12 may be in fluid communication with one or more of the fluid storage container 14 or the portable vacuum source via the conduit 17. Fluid (e.g., urine or other bodily fluids) collected in the fluid collection device 12 may be removed from the fluid collection device 12 via the conduit 17 which protrudes into an interior region of the fluid collection device 12. For example, a first open end of the conduit 17 may extend into the fluid collection device 12 to a reservoir therein. The second open end of the conduit 17 may extend into the fluid storage container 14 or the portable vacuum source 16. The suction force may be introduced into the interior region of the fluid collection device 12 via the first open end of the conduit 17 responsive to a suction (e.g., vacuum) force applied at the second end of the conduit 17. The suction force may be applied to the second open end of the conduit 17 by the portable vacuum source 16 either directly or indirectly.

The suction force may be applied indirectly via the fluid storage container 14. For example, the second open end of the conduit 17 may be disposed within the fluid storage container 14 and an additional conduit 17 may extend from the fluid storage container 14 to the portable vacuum source 16. Accordingly, the portable vacuum source 16 may apply suction to the fluid collection device 12 via the fluid storage container 14. The suction force may be applied directly via the fluid storage container 14. For example, the second open end of the conduit 17 may be disposed within the portable vacuum source 16. An additional conduit 17 may extend from the portable vacuum source 16 to a point outside of the fluid collection device 12, such as to the fluid storage container. In such examples, the portable vacuum source 16 may be disposed between the fluid collection device 12 and the fluid storage container 14.

The fluid collection device 12 may be shaped and sized to be positioned adjacent to a female urethra or have a male urethra positioned therethrough (e.g., receive a penis therein). For example, the fluid collection device 12 may include a fluid impermeable barrier at least partially defining a chamber (e.g., interior region of the fluid collection device 12) of the fluid collection device. The fluid impermeable barrier also defines an opening extending therethrough from the external environment. The opening may be positioned adjacent to a female urethra or have a male urethra positioned therethrough. The fluid collection device 12 may include a fluid permeable membrane disposed within the fluid impermeable barrier. The fluid collection device 12 may include a fluid permeable support disposed within the fluid permeable membrane. The conduit 17 may extend into the fluid collection device 12 at a first end region, through one or more of the fluid impermeable barrier, fluid permeable membrane, or the fluid permeable support to a second end region of the fluid collection device 12. Exemplary fluid collection devices for use with the systems and methods herein are described in more detail below.

In some examples, the fluid storage container 14 may include a bag (e.g., drainage bag), a bottle or cup (e.g., collection jar), or any other enclosed container for storing bodily fluid(s) such as urine. In some examples, the conduit 17 may extend from the fluid collection device and attach to the fluid storage container 14 at a first point therein. An additional conduit 17 may attach to the fluid storage container 14 at a second point thereon and may extend and attach to the portable vacuum source 16. Accordingly, a vacuum (e.g., suction) may be drawn through fluid collection device 12 via the fluid storage container 14. Fluid, such as urine, may be drained from the fluid collection device 12 using the portable vacuum source 16.

In some examples, the portable vacuum source 16 may be disposed in or on the fluid collection device 12. In such examples, the conduit 17 may extend from the fluid collection device and attach to the portable vacuum source 16 at a first point therein. An additional conduit 17 may attach to the portable vacuum source 16 at a second point thereon and may extend out of the fluid collection device 12, and may attach to the fluid storage container 14. Accordingly, a vacuum (e.g., suction) may be drawn through fluid collection device 12 via the fluid storage container 14. Fluid, such as urine, may be drained from the fluid collection device 12 using the portable vacuum source 16. The portable vacuum source 16 may include one or more of a manual vacuum pump, and electric vacuum pump, a diaphragm pump, a centrifugal pump, a displacement pump, a magnetically driven pump, a peristaltic pump, or any pump configured to produce a vacuum. The portable vacuum source 16 may provide a vacuum or suction to remove fluid from the fluid collection device 12. In some examples, the portable vacuum source 16 may be powered by one or more of a power cord (e.g., connected to a power socket), one or more batteries, or even manual power (e.g., a hand operated vacuum pump). In some examples, the portable vacuum source 16 may be sized and shaped to fit outside of, on, or within the fluid collection device 12. For example, the portable vacuum source 16 may include one or more min-iaturized pumps or one or more micro pumps. The portable vacuum sources 16 disclosed herein may include one or more of a switch, a button, a plug, a remote, or any other device suitable to activate the portable vacuum source. It should be understood that the portable vacuum sources 16 disclosed herein may provide a portable means of providing a suction or vacuum that allows use of the devices and systems herein outside of hospital or care facility environ-ments where vacuum lines are plumbed into patient rooms or large (e.g., larger or heavier than a patient can readily carry) vacuum sources are located. For example, a portable vacuum source may be small and light enough to be carried by a user (e.g., patient) or aid (e.g., nurse) during transpor-tation of the user.

Figure 2:
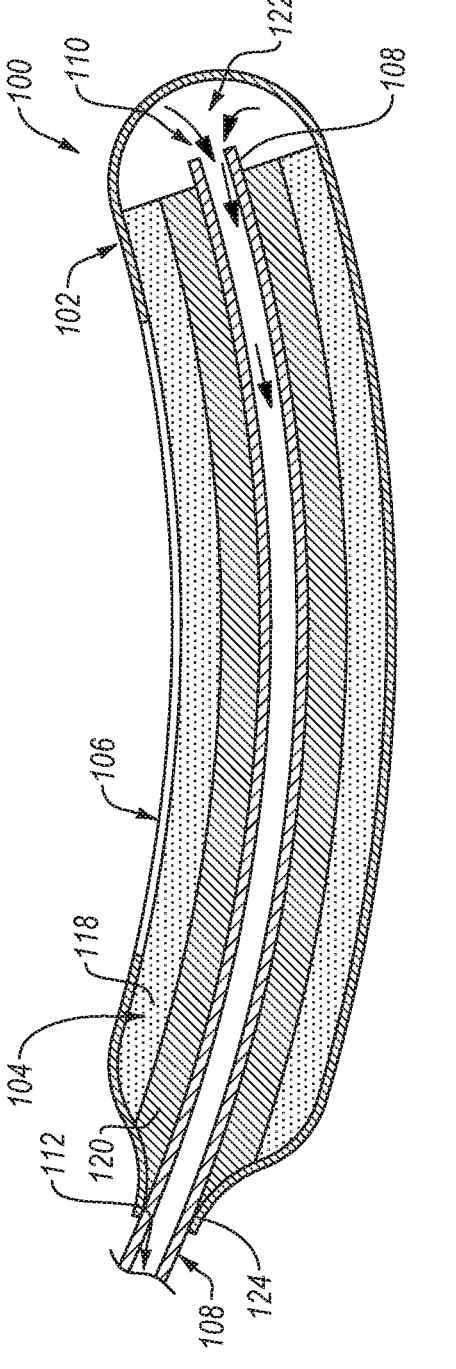
FIGS. 2-4 are schematic cross-sectional views of female fluid collection devices, according to embodiments.

FIG. 2 is a schematic cross-sectional view of a fluid collection device 100, according to an embodiment. The fluid collection device 100 is an example of a female fluid collection device 100 that is configured to receive fluid(s) from a female. The fluid collection device 100 includes a fluid impermeable barrier 102. The fluid impermeable bar-rier 102 at least partially defines a chamber 104 (e.g., interior region) and an opening 106. The opening 106 is formed in and extends through the fluid impermeable barrier 102, thereby enabling fluid(s) to enter the chamber 104 from outside of the fluid collection device 100. The opening 106 can be configured to be positioned adjacent to a female urethra. The fluid collection device 100 also includes con-duit 108 that is at least partially disposed in the chamber 104. The conduit 108 (e.g., a tube) includes an inlet 110 at a first end region and an outlet 112 at a second end region positioned downstream from the inlet 110. The conduit 108 fluidly couples an interior region of the chamber 104 with the fluid storage container (not shown) or the portable vacuum source (not shown).

In the illustrated embodiment, the conduit 108 is at least partially disposed in the chamber 104. For example, the conduit 108 may extend into the fluid impermeable barrier 102 from the first end region (e.g., proximate to the outlet 112) and may extend to the second end region (e.g., opposite the first end region) to a point proximate to a reservoir 122 such that the inlet 110 is in fluid communication with the reservoir 122. For example, in the illustrated embodiment, the inlet 110 is positioned in the reservoir 122. However, in other examples, the inlet 110 may be positioned flush with or behind an end of the fluid permeable membrane 118 that partially defines the reservoir 122. In some examples (not shown), the conduit 108 may enter the second end region and the inlet 110 of the conduit 108 may be disposed in the second end region (e.g., in the reservoir 122). The fluid collected in the fluid collection device 100 may be removed from the interior region of the chamber 104 via the conduit 108. The conduit 108 may include a flexible material such as plastic tubing (e.g., medical tubing). Such plastic tubing may include a thermoplastic elastomer, polyvinyl chloride, eth-ylene vinyl acetate, polytetrafluoroethylene, etc., tubing. In some examples, the conduit 108 may include silicon or latex. In some examples, the conduit 108 may include one or more portions that are resilient, such as to by having one or more of a diameter or wall thickness that allows the conduit to be flexible.

The fluid collection device 100 may be positioned proxi-mate to the female urethra and urine may enter the interior region of the fluid collection device 100 via the opening 106. The fluid collection device 100 is configured to receive the fluid(s) into the chamber 104 via the opening 106. For example, the opening 106 can exhibit an elongated shape that is configured to extend from a first location below the urethral opening (e.g., at or near the anus or the vaginal opening) to a second location above the urethral opening (e.g., at or near the clitoris or the pubic hair). The opening 106 can exhibit an elongated shape since the space between the legs of a female is relatively small when the legs of the female are closed, thereby only permitting the flow of the fluid(s) along a path that corresponds to the elongated shape of the opening 106 (e.g., longitudinally extending opening). The longitudinal axis or dimension of the fluid collection devices disclosed herein refers to the axis or dimension that is parallel to largest dimension of the device, such as axially along a cylindrical device as show in FIG. 2. The opening 106 in the fluid impermeable barrier 102 can exhibit a width that is measured transverse to the longitudinal direction of the fluid collection device 100 and may be at least about 10% of the circumference of the fluid collection device 100, such as about 25% to about 50%, about 40% to about 60%, about 50% to about 75%, about 65% to about 85%, or about 75% to about 100% of the circumference of the fluid collection device 100. The opening 106 can exhibit a width that is greater than 50% of the circumference of the fluid collection device 100 since the vacuum (e.g., suction) through the conduit 108 pulls the fluid into the conduit 108. In some examples, the opening 106 may be vertically oriented (e.g., having a major axis parallel to the longitudi-nal axis of the device 100). In some examples (not shown), the opening 106 may be horizontally oriented (e.g., having a major axis perpendicular to the longitudinal axis of the device 100). In an example, the fluid impermeable barrier 102 can be configured to be attached to the individual, such as adhesively attached (e.g., with a hydrogel adhesive) to the individual. According to an example, a suitable adhesive is a hydrogel layer, such as those disclosed in U.S. Patent Application Publication No. 2017/0189225, the disclosure of which is incorporated herein by reference in its entirety.

The fluid impermeable barrier 102 may also temporarily store the fluid(s in the chamber 104. For example, the fluid impermeable barrier 102 can be formed of any suitable fluid impermeable materials, such as a fluid impermeable poly-mer (e.g., silicone, polypropylene, polyethylene, polyethyl-ene terephthalate, a polycarbonate, etc.), a metal film, another suitable material, or combinations thereof. As such, the fluid impermeable barrier 102 substantially prevents the fluid(s) from exiting the portions of the chamber 104 that are spaced from the opening 106. The fluid impermeable barrier 102 can store fluid(s) in a reservoir 122 therein. The reser-voir 122 may be disposed in any portion of the interior region of the chamber 104. For example, the fluid reservoir 122 may be positioned in the second end region of the chamber 104. In an example, the fluid impermeable barrier 102 can be air permeable and fluid impermeable. In such an example, the fluid impermeable barrier 102 can be formed of a hydrophobic material that defines a plurality of pores. In an example, at least one or more portions of at least an outer surface of the fluid impermeable barrier 102 can be formed from a soft and/or smooth material, thereby reducing chaff-ing. The fluid impermeable barrier 102 may include markings thereon, such as one or more markings to aid a user in aligning the device 100 on the wearer. For example, a line on the fluid impermeable barrier 102 (e.g., opposite the opening 106) may allow a healthcare professional to align the opening 106 over the urethra of the wearer. In examples, the markings may include one or more of alignment guide or an orientation indicator, such as a stripe or hashes. Such markings may be positioned to align the device 100 to one or more anatomical features such as a pubic bone, etc.

The fluid collection device 100 can include a fluid permeable membrane 118 disposed in the chamber 104. The fluid permeable membrane 118 can cover at least a portion (e.g., all) of the opening 106. The fluid permeable membrane 118 can be configured to wick any fluid away from the opening 106, thereby preventing the fluid from escaping the chamber 104. The permeable properties referred to herein can be wicking, capillary action, diffusion, or other similar properties or processes, and are referred to herein as "permeable" and/or "wicking." Such "wicking" may not include absorption into the wicking material. The fluid permeable membrane 118 can also wick the fluid generally towards an interior of the chamber 104, as discussed in more detail below. The fluid permeable membrane 118 can include any material that can wick the fluid. For example, the fluid permeable membrane 118 can include fabric, such as a gauze (e.g., a silk, linen, polymer based materials such as polyester, or cotton gauze), another soft fabric (e.g., jersey knit fabric or the like), or another smooth fabric (e.g., rayon, satin, or the like). Forming the fluid permeable membrane 118 from gauze, soft fabric, and/or smooth fabric can reduce chaffing caused by the fluid collection device 100.

The fluid collection device 100 can include a fluid permeable support 120 disposed in the chamber 104. The fluid permeable support 120 is configured to support the fluid permeable membrane 118 since the fluid permeable membrane 118 can be formed from a foldable, flimsy, or otherwise easily deformable material. For example, the fluid permeable support 120 can be positioned such that the fluid permeable membrane 118 is disposed between the fluid permeable support 120 and the fluid impermeable barrier 102. As such, the fluid permeable support 120 can support and maintain the position of the fluid permeable membrane 118. The fluid permeable support 120 can include any material that can wick the fluid. The fluid permeable support 120 can be formed from any fluid permeable material that is less deformable than the fluid permeable membrane 118. For example, the fluid permeable support 120 can include a porous nylon structure. In an example, the fluid permeable support 120 can be omitted from the fluid collection device 100.

In an example, the fluid permeable membrane 118 and the fluid permeable support 120 can at least substantially completely fill the portions of the chamber 104 that are not occupied by the conduit 108. In another example, the fluid permeable membrane 118 and the fluid permeable support 120 may not substantially completely fill the portions of the chamber 104 that are not occupied by the conduit 108. In such an example, the fluid collection device 100 includes the reservoir 122 disposed in the chamber 104. The reservoir 122 is a substantially unoccupied portion of the chamber 104. The reservoir may be defined between the fluid impermeable barrier 102 and one or both of the fluid permeable membrane 118 and the fluid permeable support. The fluid(s) that are in the chamber 104 can flow through the fluid permeable membrane 118 and/or fluid permeable support 120 to the reservoir 122. The reservoir 122 can store at least some of the fluid(s) therein.

In an example, the reservoir 122 can be located at the portion of the chamber 104 that is closest to the inlet 110 (e.g., the second end region). However, the reservoir 122 can be located at different locations in the chamber 104. For example, the reservoir 122 can be located at the end of the chamber 104 that is closest to the outlet 112. In another example, the fluid collection device 100 can include multiple reservoirs, such as a first reservoir that is located at the portion of the chamber of the chamber 104 that is closest to the inlet 110 (e.g., second end region) and a second reservoir that is located at the portion of the of the chamber 104 that is closest to the outlet 112 (e.g., first end region). In another example, the fluid permeable support 120 is spaced from at least a portion of the conduit 108 and the reservoir 122 can be the space between the fluid permeable support 120 and the conduit 108.

In some examples, the fluid collection device 100 may be substantially cylindrical, ellipsoid, prismatic, or any other shape suitable for complementing or contouring to the vaginal region of a female subject. The cross-sectional shape of the fluid collection devices disclosed herein may include any of various shapes or sizes. For example, the cross-sectional shape (transverse to the longitudinal axis) may be substantially round (e.g., circular), elliptical, rectangular, triangular, irregular (e.g., having no specific shape), etc.

Other embodiments of fluid impermeable barriers, fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. patent application Ser. No. 15/611,587 filed on Jun. 1, 2017, the disclosure of each of which is incorporated herein, in its entirety, by this reference.

The fluid impermeable barrier 102, the fluid permeable membrane 118 and the fluid permeable support 120 can be configured to have the conduit 108 at least partially disposed in the chamber 104. For example, at least one of the fluid permeable membrane 118 and the fluid permeable support 120 can be configured to form a space that accommodates the conduit 108. In another example, the fluid impermeable barrier 102 can define an aperture 124 sized to receive the conduit 108 (e.g., at least one tube). The at least one conduit 108 can be disposed in the chamber 104 via the aperture 124. The apertures 124 can be configured to form an at least substantially fluid tight seal against the conduit 108 or the at least one tube thereby substantially preventing the fluid(s) from escaping the chamber 104. The fluid collected in the fluid collection device 100 may be removed from the interior region of the chamber 104 via the conduit 108. As shown in FIG. 2, the end of the conduit 108 may extend beyond the fluid permeable membrane 118 and/or fluid permeable support 120, such as into the reservoir 122. In some examples, the inlet 110 may not extend into the reservoir 122. In such examples, the inlet 110 may be disposed within the wicking material (fluid permeable membrane 118 and/or fluid permeable support 120) or a terminal end thereof. For example, an end of the conduit 108 may be coextensive with or recessed within the fluid permeable membrane 118 and/or fluid permeable support 120.

As previously discussed, the conduit 108 is configured to be coupled to and at least partially extend between one or more of the fluid storage container (not shown) and the portable vacuum source (not shown). In an example, the conduit 108 is configured to be directly connected to the portable vacuum source (not shown). In such an example, the conduit 108 can extend from the fluid impermeable barrier 102 by at least one foot, at least two feet, at least three feet, or at least six feet. In another example, the conduit 108 is configured to be indirectly connected to at least one of the fluid storage container (not shown) and the portable vacuum source (not shown). In some examples, the conduit is secured to a wearer's skin with a catheter securement device, such as a STATLOCK® catheter securement device available from C. R. Bard, Inc., including but not limited to those disclosed in U.S. Pat. Nos. 6,117,163; 6,123,398; and 8,211, 063, the disclosures of which are all incorporated herein by reference in their entirety.

The inlet 110 and the outlet 112 are configured to fluidly couple (e.g., directly or indirectly) the portable vacuum source (not shown) to the chamber 104 (e.g., the reservoir 122). In an example, the inlet 110 and/or the outlet 112 can form a male connector. In another example, the inlet 110 and/or the outlet 112 can form a female connector. In an example, the inlet 110 and/or the outlet 112 can include ribs that are configured to facilitate secure couplings. In an example, the inlet 110 and/or the outlet 112 can form a tapered shape. In an example, the inlet 110 and/or the outlet 112 can include a rigid or flexible material.

Locating the inlet 110 at or near a gravimetrically low point of the chamber 104 enables the conduit to receive more of the fluid(s) than if inlet 110 was located elsewhere and reduce the likelihood of pooling (e.g., pooling of the fluid(s) can cause microbe growth and foul odors). For instance, the fluid(s) in the fluid permeable membrane 118 and the fluid permeable support 120 can flow in any direction due to capillary forces. However, the fluid(s) may exhibit a preference to flow in the direction of gravity, especially when at least a portion of the fluid permeable membrane 118 and/or the fluid permeable support 120 is saturated with the fluid(s). Accordingly, one or more of the inlet 110 or the reservoir 122 may be located in the fluid collection device in a position expected to be the gravimetrically low point in the fluid collection device when worn by a user.

As the portable vacuum source (FIG. 1) applies a vacuum/ suction in the conduit 108, the fluid(s) in the chamber 104 (e.g., at the second end region such as in the reservoir 122) may be drawn into the inlet 110 and out of the fluid collection device 100 via the conduit 108. In some examples, the conduit may be frosted or opaque (e.g., black) to obscure visibility of the fluid(s) therein.

In an example, the conduit 108 is configured to be at least insertable into the chamber 104. In such an example, the conduit 108 can include one or more markers (not shown) on an exterior thereof that are configure to facilitate insertion of the conduit 108 into the chamber 104. For example, the conduit 108 can include one or more markings thereon that are configured to prevent over or under insertion of the conduit 108, such as when the conduit 108 defines an inlet 110 that is configured to be disposed in or adjacent to the reservoir 122. In another example, the conduit 108 can include one or more markings thereon that are configured to facilitate correct rotation of the conduit 108 relative to the chamber 104. In an example, the one or more markings can include a line, a dot, a sticker, or any other suitable marking.

In an example, one or more components of the fluid collection device 100 can include an antimicrobial material, such as an antibacterial material where the fluid collection device may contact the wearer or the bodily fluid of the wearer. The antimicrobial material can include an antimicrobial coating, such as a nitrofurazone or silver coating. The antimicrobial material can inhibit microbial growth, such as microbial growth due to pooling or stagnation of the fluid(s). In an example, one or more components (e.g., impermeable barrier 102, conduit 108, etc.) of the fluid collection device 100 can include an odor blocking or absorbing material such as a cyclodextrine containing material or a thermoplastic elastomer (TPE) polymer.

Figure 3:
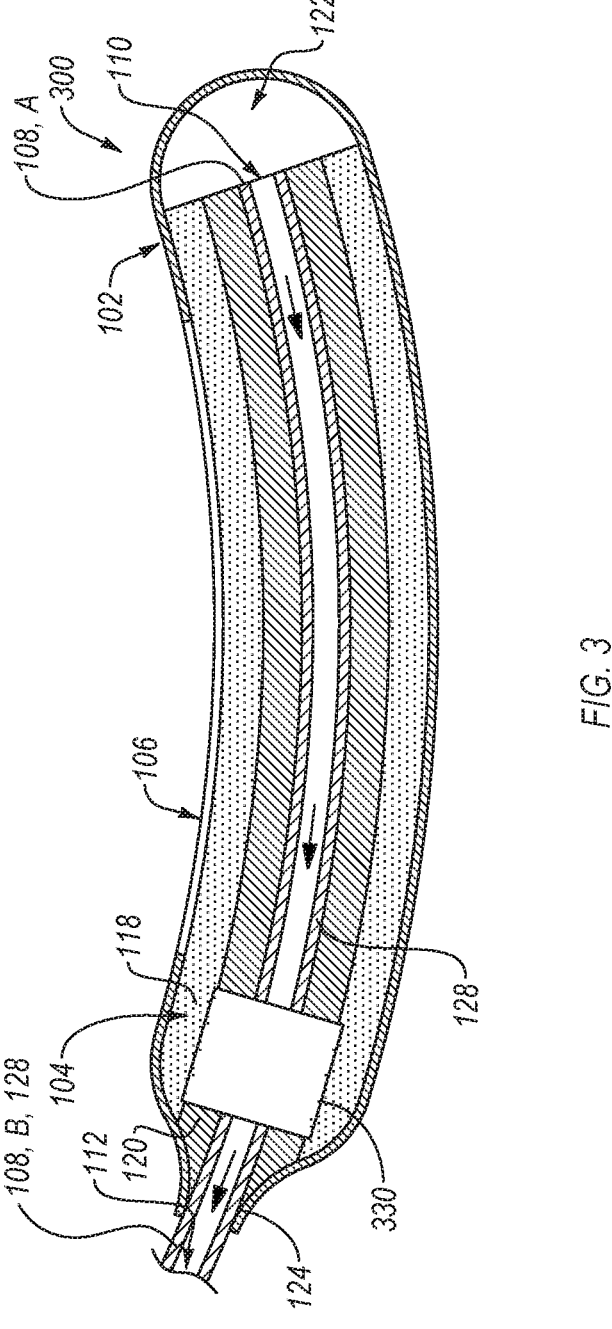

FIG. 3 is a schematic cross-sectional view of a fluid collection device 300, according to an embodiment. The fluid collection device 300 may include the portable vacuum source 330 disposed therein. Except as otherwise disclosed herein, the fluid collection device 300 can be the same as or substantially similar to the fluid collection device 100 of FIG. 2, in one or more aspects. For example, the fluid collection device 300 can include the fluid impermeable barrier 102 that defines the chamber 104 and the opening 106. The fluid collection device 300 also includes at least one of the fluid permeable membrane 118, the fluid permeable support 120, and the reservoir 122 disposed in the chamber 104.

The fluid collection device 300 includes the conduit 108 that is at least partially disposed in the chamber 104. The conduit 108 can include one or more walls that define an inlet 110 and the outlet 112. The inlet 110 enables at least some of the fluids that are present in the chamber 104 to enter the conduit 108. In an example, the conduit 108 can be configured to have the inlet 110 located at, near, or spaced at a gravimetrically low point of the chamber 104. In an example, the conduit 108 can be configured to have the at least one inlet 110 disposed in or adjacent to the reservoir 122.

The conduit 108 can be in fluid communication with the interior region of the chamber 104 via the fluid impermeable barrier 102. As such, the fluid impermeable barrier 102 can define an aperture 124. In an example, as illustrated, the aperture 124 enables the conduit 108 to extend outwardly from the chamber 104 when the conduit 108 is only partially disposed in the chamber 104. In some examples, the conduit 108 may include a plurality of separate sections. For example and as shown, the conduit 108 may include a first section A and a second section B. The first section A may include the inlet 110 extending from the distal end (e.g., first end region) to the portable vacuum source 330 and the B section may extend from the portable vacuum source 330 out of the aperture 124, such as to a fluid storage container (not shown).

The portable vacuum source 330 may include a pump, such as any of the portable vacuum pumps disclosed herein. For example, the portable vacuum source 330 may include a manual vacuum pump, a diaphragm pump, a centrifugal pump, a displacement pump, a magnetically driven pump, a peristaltic pump, or any pump configured to produce suction, a vacuum, or otherwise move a fluid. The portable vacuum source 330 may be sized to fit in the chamber 104 inside of the fluid impermeable barrier 102. In some examples, the portable vacuum source 330 may be sealed in a fluid tight housing or container. The portable vacuum source 330 may apply a vacuum (e.g., suction) in the A section of the conduit 108 effective to suction fluid from the chamber 104. The fluid may travel through the A section to the B section (e.g., through the portable vacuum source 330) and out of the fluid collection device 300 via the B section by flow induced by the vacuum or suction applied by the portable vacuum source 330. For example, the portable vacuum source 330 may include a centrifugal pump and an impeller therein may draw the fluid from the chamber 104 via the inlet 110 and force the fluid out of the chamber 104 via the B section of the conduit 108. Each of the A second and the B section of the conduit 108 may be fluidly coupled (e.g., sealed) to the portable vacuum source 330.

In some examples, the portable vacuum source 330 and the conduit 108 can be integrally formed together (e.g., exhibit single piece construction).

Figure 4:
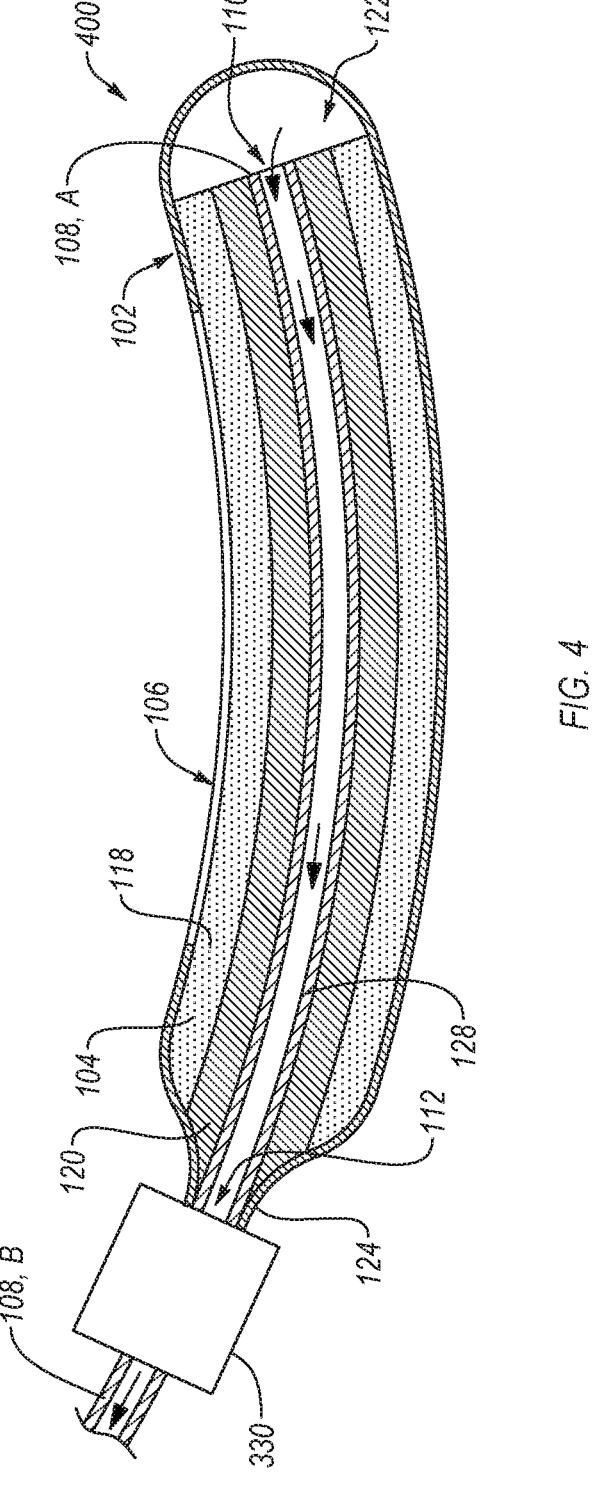

FIG. 4 is a schematic cross-sectional view of a fluid collection device 400, according to an embodiment. The fluid collection device 400 may include the portable vacuum source 330 disposed thereon. Except as otherwise disclosed herein, the fluid collection device 400 can be the same as or substantially similar to the fluid collection device 100 of FIG. 2, in one or more aspects. For example, the fluid collection device 400 can include the fluid impermeable barrier 102 that defines the chamber 104 and the opening 106. The fluid collection device 400 also includes at least one of the fluid permeable membrane 118, the fluid permeable support 120, and the reservoir 122 disposed in the chamber 104. The portable vacuum source 330 may be attached to the fluid collection device 400 at the fluid impermeable barrier 102.

The fluid collection device 400 includes the conduit 108 that is at least partially disposed in the chamber 104. The conduit 108 can include one or more walls that define an inlet 110 and the outlet 112. The inlet 110 enables at least some of the fluids that are present in the chamber 104 to enter the conduit 108. In an example, the conduit 108 can be configured to have the inlet 110 located at, near, or spaced at a gravimetrically low point of the chamber 104. In an example, the conduit 108 can be configured to have the at least one inlet 110 disposed in or adjacent to the reservoir 122.

The conduit 108 can be in fluid communication with the interior region of the chamber 104 via the fluid impermeable barrier 102. As such, the fluid impermeable barrier 102 can define an aperture 124. In an example, as illustrated, the aperture 124 enables the conduit 108 to extend outwardly from the chamber 104 when the conduit 108 is only partially disposed in the chamber 104. In some examples, the conduit 108 may include a plurality of separate sections. For example and as shown, the conduit 108 may include the first section A and the second section B. The first section A may include the inlet 110 extending from the distal end (e.g., first end region), out of the aperture 124, to the portable vacuum source 330 mounted thereto. The portable vacuum source 330 may be mounted to the outer surface of the fluid collection device 400, such as on the fluid impermeable barrier 102. The B section may be attached to and extend from the portable vacuum source 330, such as to a fluid storage container (not shown).

The portable vacuum source 330 may include any of the portable vacuum pumps disclosed herein such as a manual vacuum pump, a diaphragm pump, a centrifugal pump, a displacement pump, a magnetically driven pump, a peristaltic pump, or any pump configured to produce a vacuum. The portable vacuum source 330 may be sized to fit in the chamber 104 inside of the fluid impermeable barrier 102. In some examples, the portable vacuum source 330 may be sealed in a fluid tight housing or container. The portable vacuum source 330 may apply a vacuum (e.g., suction) in the A section of the conduit 108 effective to suction fluid from the chamber 104. The fluid may travel through the A section out of the fluid collection device 400 to the portable vacuum source 330. The fluid may be removed from the portable vacuum source 330 via the B section by flow induced by the vacuum or suction applied by the portable vacuum source 330. For example, the portable vacuum source 330 may include a centrifugal pump and an impeller therein may draw the fluid from the chamber 104 via the inlet 110 and suction the fluid out of the chamber 104 via the portable vacuum source 330 to the B section of the conduit 108. Each of the A section and the B section of the conduit 108 may be fluidly coupled (e.g., sealed) to the portable vacuum source 330. In some examples, the portable vacuum source 330 and the conduit 108 (e.g., one or both of the A section or the B section) can be integrally formed together to exhibit single piece construction. The female fluid collection devices disclosed herein may also include one or more vacuum relief holes in the fluid impermeable barrier 102 to control an amount of suction or vacuum in the chamber 104. The vacuum relief hole may be positioned at any point on the fluid permeable membrane, such as at an intermediate point between the reservoir 122 and the outlet 112. Such vacuum relief holes may allow the chamber 104 to remain substantially at atmospheric pressure to prevent the fluid collection devices from deforming under vacuum force.

Figure 5:
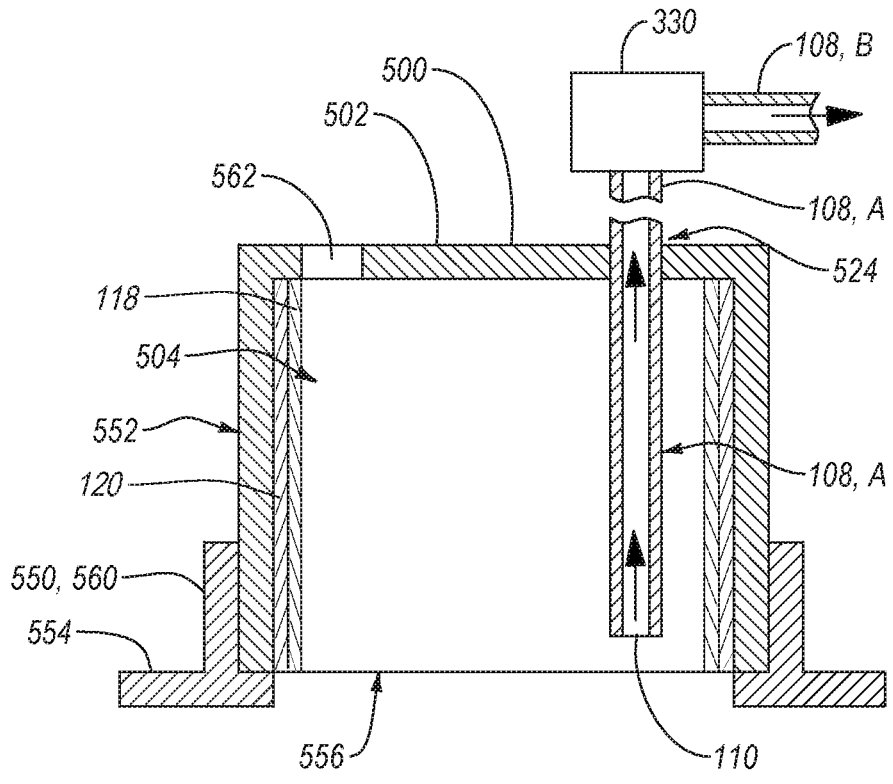
FIGS. 5-7 are schematic cross-sectional views of male fluid collection devices, according to embodiments.
Figure 6:
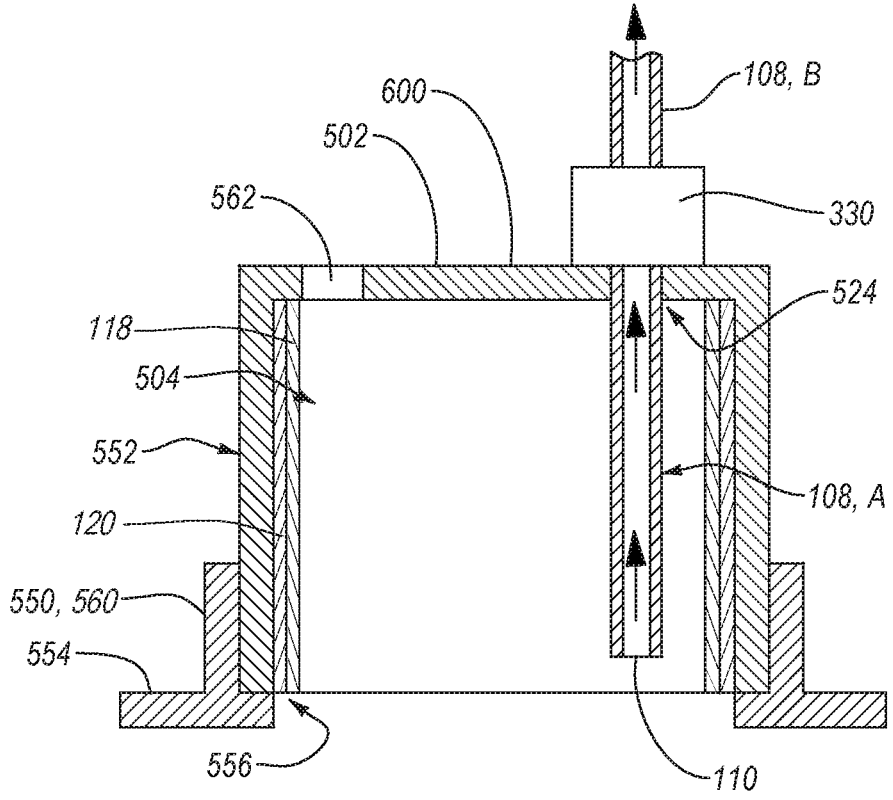
Figure 7:
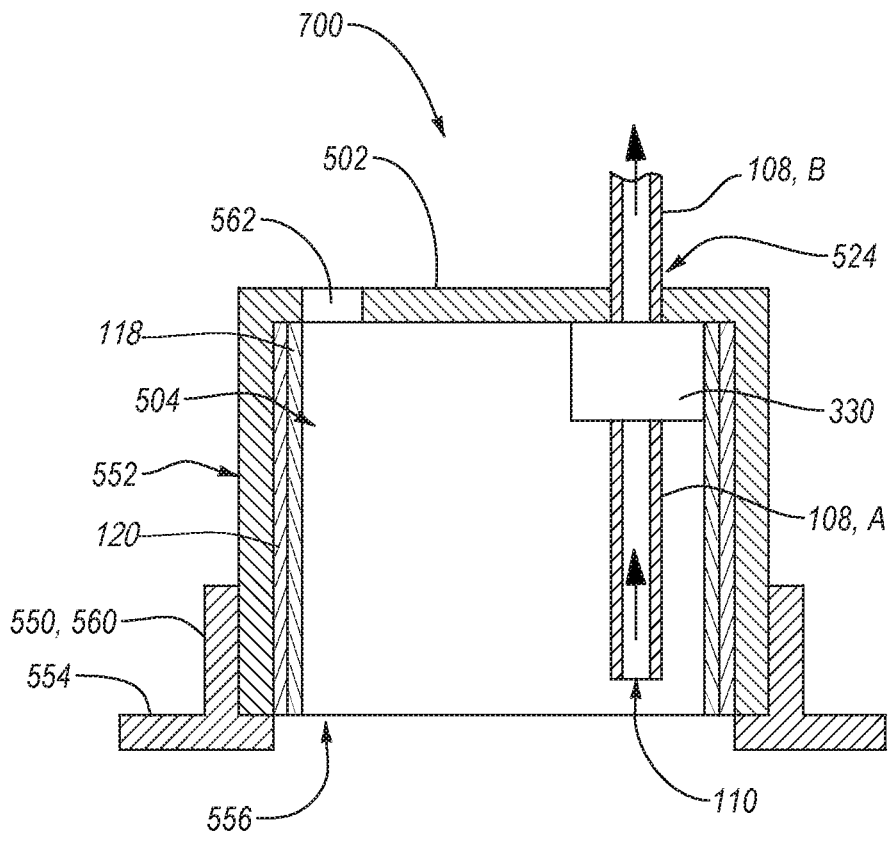

The fluid collection devices shown in FIGS. 2-4 are examples of female fluid collection devices that are configured to collect fluid(s) from females (e.g., collect urine from a female urethra). However, the fluid collection devices, systems, and methods disclosed herein can include male fluid collection devices shaped, sized, and otherwise configured to collect fluid(s) from males (e.g., collect urine from a male urethra). FIGS. 5-7 are schematic cross-sectional views of male fluid collection devices 500, 600, and 700, according to different embodiments.

Referring to FIG. 5, the fluid collection device 500 includes a receptacle 550 and a cup portion 552. The receptacle 550 is sized, shaped, and made of a material to be coupled to skin that surrounds the male urethra and have the male urethra positioned therethrough. For example, the receptacle 550 can include an annular base 554 that defines an opening 556 in the receptacle 550. The annular base 554 is sized and shaped to be positioned around the male urethra (e.g., positioned around and/or over the penis) and the opening 556 can be configured to have the male urethra positioned therethrough. The annular base 554 can also be sized, shaped, made of a material, or otherwise configured to be coupled (e.g., adhesively attached, such as with a hydrogel adhesive) to the skin around the male urethra (e.g., around the penis). In an example, the annular base 554 can exhibit the general shape of the skin surface that the annular base 554 is selected to be coupled with and/or can be flexible thereby allowing the annular base 554 to conform to any shape of the skin surface. The receptacle 550 also defines a hollowed region that is configured to receive (e.g., seal against) the cup portion 552. For example, the receptacle 550 can include a flange 560 that extends upwardly from the annular base 554. The flange 560 may be tall enough to prevent the cup portion 552 from being accidentally removed from the receptacle 550 (e.g., at least 0.5 cm tall, 1 cm tall, at least 2 cm tall, or at least 5 cm tall). In some examples, the annular base 554 is optional. For example, the receptacle 550 may only include the flange 554. In some examples (not shown), the fluid collection device may have a one piece design, with the cup portion 552 and the receptacle 550 being a single piece. In some examples, the receptacle 550 is optional.

The cup portion 552 includes (e.g., may be formed from) a fluid impermeable barrier 502 that is sized and shaped to fit into the hollowed region of the receptacle 550. The cup portion 552 may be shaped to retain a fluid therein. For example, the fluid impermeable barrier 502 may define the cup portion 552, such as forming a substantially tubular (e.g., cylindrical) body having an enclosed end as illustrated in FIG. 5. Accordingly, the cup portion 552 may have a generally cupped shape with a chamber 504 therein. The fluid impermeable barrier 502 may be similar or identical to the fluid impermeable barrier 102, in one or more aspects. The fluid impermeable barrier 502 partially defines the chamber 504. The fluid impermeable barrier 502 may also define an opening 556 extending through the fluid impermeable barrier 502 that is configured to have a male urethra positioned therethrough. The fluid impermeable barrier 502 may also include at least one passageway 562 (e.g., vacuum relief hole) that allows the chamber 504 to remain substantially at atmospheric pressure. The at least one passageway 562 may be located at any point on the cup portion 552, such as near or nearer the opening 556. The cup portion 552 also includes at least a portion of the conduit 108 therein, such as at least partially disposed in the chamber 504. For example, the conduit 108 may extend from the cup portion 552 to a region at least proximate to the opening 556. The region proximate to the opening 556 may be disposed near or on the skin around the male urethra (e.g., on the penis). Accordingly, when a patient lays on their back, fluid (e.g., urine) may aggregate near the opening 556 against the skin of the subject. The fluid may be removed from the chamber 504 via the conduit 108. In some examples, the cup portion 552 of the fluid impermeable barrier 502 may be constructed of a material and/or have a thickness that allows the cup portion 552 to collapse when placed under vacuum, such as to remove air around a penis in the fluid collection device 500 during use. In such examples, the conduit 108 may extend only into the chamber 504 at the aperture 524 (e.g., not through to the area adjacent the opening). In such examples, urine may be collected and removed from the fluid collection device 500 at the end nearest the aperture 524. In such examples, the at least one passageway may be located nearest the opening 556.

The fluid collection device 500 may include the fluid permeable membrane 118. The fluid permeable membrane 118 may be disposed between the fluid impermeable barrier 502 of the cup portion 552 and a penis inserted into the chamber 504. The fluid collection device 500 may include a fluid permeable support 120. The fluid permeable support 120 may be positioned between the cup portion 552 and a penis inserted into the chamber 504, such as between the fluid permeable membrane 118 and the fluid impermeable barrier 502. The sidewalls or the end of the chamber 504 may be covered with one or both the fluid permeable membrane 118 or the fluid permeable support 120.

In some examples, the portable vacuum source 330 may be remotely located from the cup portion 552. In such examples, the conduit 108 may extend out of and away from the cup portion 552 to the portable vacuum source 330. In some examples, the conduit 108 may include one or more sections. For example and as shown, the conduit 108 may include an A section and a B section. The A section may extend from portable vacuum source 330 through the cup portion 552 via the aperture 524 to the region at least proximate to the opening 556. The inlet 110 of the conduit is in fluid communication with the portable vacuum source 330. The outlet (not shown) may be in fluid communication with a fluid storage container (not shown) through the conduit 108 in the direction shown by the arrows. The fluid impermeable barrier 502 may include at least one aperture 524 that is sized and shaped to receive and seal against the conduit 108, such as within the chamber 504. Accordingly, the interior region of the chamber 504 may be in fluid communication with the portable vacuum source 330 via the conduit 108. As the portable vacuum source 330 applies a vacuum/suction in the direction of the arrows in FIG. 5, the fluid in the chamber 504 may be removed through the conduit 108. In some examples, the fluid may be pumped through the portable vacuum source 330 into the B section of the conduit 108. The B section of the conduit may be in fluid communication with a fluid storage container (not shown) into which the fluid may be deposited.

In some examples, the fluid storage container (not shown) may be disposed between the portable vacuum source 330 and the fluid collection device 500. In such examples, the A section of the conduit 108 may extend between the fluid collection device and the fluid storage device, the B section of the conduit 108 may extend between the fluid storage device and the portable vacuum source 330. The A and B sections of the conduit 108 and the fluid storage container may fluidly couple the portable vacuum source 330 to the fluid collection device 500. In such examples, the fluid may be suctioned from the chamber 504 into the inlet 510 and the fluid storage container (not shown) via the vacuum/suction induced by the portable vacuum source 330 through the fluid storage device.

In an example, portions of the chamber 504 may be substantially empty due to the varying sizes and rigidity of the male penis. However, in some examples, the outermost regions of the chamber 504 (e.g., periphery of the interior regions of the cup portion 552) can include a porous material (e.g., one or more of the fluid permeable membrane 118 and fluid permeable support 120, FIG. 2) positioned (e.g., at the end of the cavity) configured to blunt a stream of urine from the male urethra thereby limiting splashing and/or to direct the fluid(s) to a selected region of the chamber 504. Since the chamber 504 is substantially empty (e.g., substantially all of the chamber 504 forms a reservoir), the fluids are likely to pool at a gravimetrically low point of the chamber 504. The gravimetrically low point of the chamber 504 can be at an intersection of the skin of an individual and the fluid collection device 500, a corner formed in the cup portion 552, or another suitable location depending on the orientation of the wearer. The inlet 110 of the conduit 108 can be positioned to be adjacent or proximate to the gravimetrically low point of the chamber 504, such as adjacent to the annular base 554. For example, the inlet 110 may be co-extensive with or offset from the opening 556. In examples, the inlet may be positioned adjacent to the terminal end of the cup portion 552 (e.g., substantially opposite the opening).

During operation, a male using the fluid collection device 500 can discharge fluid(s) (e.g., urine) into the chamber 504. The fluid(s) can pool or otherwise be collected in the chamber 504. At least some of the fluid(s) can enter the interior of the conduit 108 via the inlet 110. The fluid may be drawn out of the fluid collection device 500 via the vacuum/suction provided by the portable vacuum source 330. In some examples, during operation, the passageway 562 may substantially maintain the pressure in the chamber 504 at atmospheric pressure even though fluid is introduced into and subsequently removed from the chamber 504.

In some examples, the portable vacuum source 330 may be located on the cup portion 552. FIG. 6 illustrates a fluid collection device 600 that, except as otherwise disclosed herein, is the same as or substantially similar to the fluid collection device 500 of FIG. 5, in one or more aspects. For example, the components of the fluid collection device 600 may be identical to the components of the fluid collection device 500 described above. Referring to FIG. 6, the fluid collection device 600 includes the portable vacuum source 330, the receptacle 550, the cup portion 552, and the conduit 108. As shown, the portable vacuum source 330 may be affixed to the fluid collection device 500 such as on the fluid impermeable barrier 102 defining the cup portion 552 or the receptacle 550. In such examples, the B portion of the conduit 108 may extend away from the fluid collection device 500.

The conduit 108 may extend from the chamber 504 of the cup portion 552 to the portable vacuum source 330. In some examples, the conduit 108 may include one or more sections. For example and as shown, the conduit 108 may include an A section and a B section. The A section may extend from portable vacuum source 330 through the cup portion 552 via the aperture 524 to the region at least proximate to the opening 556. The inlet 110 of the conduit is in fluid communication with the portable vacuum source 330. The outlet (not shown) may be in fluid communication with a fluid storage container (not shown) through the conduit 108 in the direction shown by the arrows. The fluid impermeable barrier 502 may include at least one aperture 524 that is sized and shaped to receive and seal against the conduit 108, such as within the chamber 504. Accordingly, the interior region of the chamber 504 may be in fluid communication with the portable vacuum source 330 via the conduit 108. As the portable vacuum source 330 applies a vacuum/suction in the direction of the arrows in FIG. 6, the fluid in the chamber 504 may be removed through the conduit 108. In some examples, the fluid may be pumped through the portable vacuum source 330 into the B section of the conduit 108. The B section of the conduit may be in fluid communication with a fluid storage container (not shown) into which the fluid may be deposited.

In some examples, the portable vacuum source 330 may be disposed between the fluid storage device (not shown) and the fluid collection device 600. In such examples, the A section of the conduit 108 may extend between the fluid collection device 600 and the portable vacuum source 330, the B section of the conduit 108 may extend between the portable vacuum source 330 and the fluid storage container. The A section of the conduit 108 may fluidly couple the portable vacuum source 330 to the fluid collection device 600. In such examples, the fluid may be suctioned from the chamber 504 into the inlet 510 through the portable vacuum source 330 to the fluid storage container (not shown) via the vacuum/suction induced by the portable vacuum source 330. In some examples, the fluid storage container may be located in the chamber 504, on the cup portion 552, or remote from the cup portion 552. In some examples, the fluid storage container (not shown) may be disposed between the portable vacuum source 330 and the fluid collection device 600.

In an example, portions of the chamber 504 of the fluid collection device 600 may be substantially empty or can include a porous material configured to blunt a stream of urine from the male urethra. Since the chamber 504 of the fluid collection device 600 is substantially empty, the fluid(s) are likely to pool at a gravimetrically low point of the chamber 504. The inlet 110 of the conduit 108 can be positioned to be adjacent or proximate to the gravimetrically low point of the chamber 504 of the fluid collection device 600.

During operation, a male using the fluid collection device 600 can discharge fluid(s) (e.g., urine) into the chamber 504. The fluid(s) can pool or otherwise be collected in the chamber 504. At least some of the fluid(s) can enter the interior of the conduit 108 via the inlet 110. The fluid may be drawn out of the fluid collection device 600 via the vacuum/suction provided by the portable vacuum source 330. In some examples, during operation, the passageway 562 may substantially maintain the pressure in the chamber 504 at atmospheric pressure even though fluid is introduced into and subsequently removed from the chamber 504.

In some examples, the portable vacuum source 330 may be located in the cup portion 552. FIG. 7 illustrates a fluid collection device 700 that, except as otherwise disclosed herein, is the same as or substantially similar to the fluid collection device 500 of FIG. 5 or 600 of FIG. 6 in one or more aspects. For example, the components of the fluid collection device 700 may be identical to the components of the fluid collection device 500 or 600 described above. Referring to FIG. 7, the fluid collection device 700 includes the portable vacuum source 330, the receptacle 550, the cup portion 552, and the conduit 108. As shown, the portable vacuum source 330 may be affixed to the fluid collection device 700 such as on the cup portion 552 or the receptacle 550. In such examples, the B portion of the conduit 108 may extend out of and away from the fluid collection device 700.

The conduit 108 may extend from the chamber 504 of the cup portion 552 to the portable vacuum source 330. In some examples, the conduit 108 may include one or more sections. For example and as shown, the conduit 108 may include an A section and a B section. The A section may extend from portable vacuum source 330 in the cup portion 552 to the region at least proximate to the opening 556. The inlet 110 of the conduit is in fluid communication with the portable vacuum source 330. The outlet (not shown) may be in fluid communication with a fluid storage container (not shown) through the conduit 108 in the direction shown by the arrows. The fluid impermeable barrier 502 may include at least one aperture 524 that is sized and shaped to receive and seal against the conduit 108, such as within the chamber 504. Accordingly, the interior region of the chamber 504 may be in fluid communication with the portable vacuum source 330 via the conduit 108. As the portable vacuum source 330 applies a vacuum/suction in the direction of the arrows in FIG. 7, the fluid in the chamber 504 may be removed through the conduit 108. In some examples, the fluid may be pumped through the portable vacuum source 330 into the B section of the conduit 108. The B section of the conduit may extend out of the aperture 524 to a fluid storage container (not shown) fluidly coupled thereto, into which the fluid may be deposited.

In some examples, the portable vacuum source 330 may be disposed between the fluid storage device (not shown) and the fluid collection device 700. In such examples, the A section of the conduit 108 may extend between the chamber 504 of the fluid collection device 700 and the portable vacuum source 330, the B section of the conduit 108 may extend between the portable vacuum source 330 and the fluid storage container. The A section of the conduit 108 may fluidly couple the portable vacuum source 330 to the fluid collection device 700. In such examples, the fluid may be suctioned from the chamber 504 into the inlet 510 through the portable vacuum source 330 to the fluid storage container (not shown) via the vacuum/suction induced by the portable vacuum source 330. In some examples, the fluid storage container may be located in the chamber 504, on the cup portion 552, or remote from the cup portion 552. In some examples, the fluid storage container (not shown) may be disposed between the portable vacuum source 330 and the fluid collection device 700.

In an example, portions of the chamber 504 of the fluid collection device 700 may be substantially empty due to the varying sizes and rigidity of the male penis. However, in some examples, the outermost regions of the chamber 504 can include a porous material configured to blunt a stream of urine from the male urethra. Since the chamber 504 is substantially empty, the fluids are likely to pool at a gravimetrically low point of the chamber 504. The inlet 110 of the conduit 108 can be positioned to be adjacent or proximate to the gravimetrically low point of the chamber 504 of the fluid collection device 700.

During operation, a male using the fluid collection device 700 can discharge fluid(s) (e.g., urine) into the chamber 504. The fluid(s) can pool or otherwise be collected in the chamber 504. At least some of the fluid(s) can enter the interior of the conduit 108 via the inlet 110. The fluid may be drawn out of the fluid collection device 700 via the vacuum/suction provided by the portable vacuum source 330. In some examples, during operation, the passageway 562 may substantially maintain the pressure in the chamber 504 at atmospheric pressure even though fluid is introduced into and subsequently removed from the chamber 504.

In any of the examples disclosed herein, the conduits 108 may include or be operably coupled to a flow meter (not shown) to measure the flow of fluid(s) therein, one or more securement devices (e.g., a STATLOCK® securement device, not shown) or fittings to secure the conduit 108 to one or more components of the systems or devices disclosed herein (e.g., portable vacuum source or fluid storage container), or one or more valves to control the flow of fluid(s) in the systems and devices herein. In any of the examples disclosed herein, the conduits 108 or other portions of the devices and systems may include a port for inserting one or more testing devices to determine if the collected urine indicates an onset of an infection (e.g., urinary tract infection or kidney infection). For example, one or more testing strips or sticks may be inserted through a port in the conduit 108.

In an example, at least one of portion of the conduit 108 of the fluid collection devices or systems herein can be formed of an at least partially opaque material which can obscure the fluids that are present therein. For example, the B section of the conduits 108 disclosed herein may be formed of an opaque material or translucent material while the A section may be formed of a transparent material or translucent material. In some examples, the B section may include transparent or translucent material. Unlike the opaque or nearly opaque material, the translucent material allows a user of the devices and systems herein to visually identify fluid(s) or issues that are inhibiting the flow of fluid(s) within the conduit 108.

In any of the example, systems or devices disclosed herein, the system of fluid collection device may include moisture sensors (not shown) disposed inside of the chamber of the fluid collection device. In such examples, the moisture sensor may be operably coupled to a controller or directly to the portable vacuum source, and may provide electrical signals indicating that moisture is or is not detected in one or more portions of the chamber. The moisture sensor(s) may provide an indication that moisture is present, and responsive thereto, the controller or portable vacuum device may direct the initiation of suction to the chamber to remove the fluid therefrom. Suitable moisture sensors may include capacitance sensors, volumetric sensors, potential sensors, resistance sensors, frequency domain reflectometry sensors, time domain reflectometry sensors, or any other suitable moisture sensor. In practice, the moisture sensors may detect moisture in the chamber and may provide a signal to the controller or portable vacuum source to activate the portable suction device.

FIG. 8 is a flow diagram of a method 800 to use any of the fluid collection devices and/or fluid collection systems disclosed herein, according to an example. The method 800 can include act 810, which recites "positioning an opening of a fluid collection device adjacent to a female urethra or around a male urethra, the opening defined by a fluid impermeable barrier of the fluid collection device." Act 810 may be followed by act 820, which recites "receiving fluid from the female urethra or the male urethra into a chamber of the fluid collection device, the chamber of the fluid collection device at least partially defined by the fluid impermeable barrier." Act 820 may be followed by act 830, which recites "applying suction with a portable vacuum source effective to suction the fluid from the chamber via a conduit disposed therein and in fluid communication with the portable vacuum source."

Acts 810, 820, 830 of the method 800 are for illustrative purposes. For example, the act 810, 820, 830 of the method 800 can be performed in different orders, split into multiple acts, modified, supplemented, or combined. In an example, one or more of the acts 810, 820, 830 of the method 800 can be omitted from the method 800. Any of the acts 810, 820, or 830 can include using any of the fluid collection devices or systems disclosed herein.

Act 810 recites "positioning an opening of a fluid collection device adjacent to a female urethra or around a male urethra, the opening defined by a fluid impermeable barrier of the fluid collection device." In some examples, act 810 can include positioning the opening of a female fluid collection device such that the fluid permeable membrane of the female fluid collection device abuts or is positioned proximate to the female urethra. In some examples, act 810 can include positioned a receptacle of a male fluid collection device around (e.g., over) the male urethra such that the male urethra is positioned in the receptacle. In such an example, act 810 can include positioning a cup portion of the male fluid collection device in a hollowed region of the receptacle such that the male urethra is positioned through an opening of the cup portion of the male fluid collection device and into the interior cavity of the male fluid collection device. In some examples, the act 810 may include positioning a penis within the fluid collection device, such as in the chamber thereof. In some examples, positioning an opening of a fluid collection device adjacent to a female urethra or around a male urethra may include positioning the opening over the female urethra, such as positioning a longitudinally extending opening of the fluid collection device over the female urethra.

Act 820 recites "receiving fluid from the female urethra or the male urethra into a chamber of the fluid collection device, the chamber of the fluid collection device at least partially defined by the fluid impermeable barrier." For example, act 820 can include wicking the fluid(s) away from the opening using a fluid permeable membrane and a fluid permeable support. In some examples, act 820 can include receiving the fluid(s) into the chamber of the cup portion of the male fluid collection device. In either example, act 820 can include flowing the fluid towards a portion of the chamber that is in fluid communication with an inlet of a conduit in fluid communication a vacuum source. For instance, act 820 can include flowing the fluid(s) to a substantially unoccupied portion of the chamber (e.g., a reservoir), to a gravimetrically low point of the chamber, etc. In some examples, receiving fluid(s) from the female urethra or the male urethra into a chamber of the fluid collection device may include wicking the fluid (e.g., urine) into the chamber via the fluid permeable membrane and fluid permeable support of the fluid collection device. For example, wicking the fluid into the chamber via the fluid permeable membrane and fluid permeable support may include wicking urine into a reservoir in the fluid collection device.

Act 830 recites, "applying suction with a portable vacuum source effective to suction the fluid(s) from the chamber via a conduit disposed therein and in fluid communication with the portable vacuum source." In some examples, applying suction with a portable vacuum source effective to suction the fluid(s) from the chamber via a conduit disposed therein and in fluid communication with the portable vacuum source can include using any of the portable vacuum sources disclosed herein. In an example, act 830 can include activating the portable vacuum source (e.g., portable suction device) in fluid communication with the inlet of the conduit in the fluid collection device. In some examples, activating the portable vacuum source in fluid communication with the inlet of the conduit in the fluid collection device can include supplying power to the portable vacuum source by one or more of flipping an on/off switch, pressing a button, plugging the portable vacuum source into a power outlet, putting batteries into the portable vacuum source, etc. In some examples, the portable vacuum source may include a hand operated vacuum pump and applying suction with a portable vacuum source may include manually operating the hand operated vacuum pump effective to suction the fluid(s) from the chamber via the conduit disposed therein that is in fluid communication with the portable vacuum source.

In some examples, applying suction with a portable vacuum source effective to suction the fluid(s) from the chamber via a conduit disposed therein and in fluid communication with the portable vacuum source can be effective to remove at least some fluid (e.g., urine) from the chamber (e.g., interior region) of the fluid collection device. In some examples, applying suction with a portable vacuum source effective to suction the fluid(s) from the chamber via a conduit disposed therein and in fluid communication with the portable vacuum source can be effective to transfer at least some of the fluid from the chamber of the fluid collection device to a fluid storage container (e.g., a bottle or bag). In some examples, applying suction with a portable vacuum source effective to suction the fluid(s) from the chamber may include removing fluid from one or more of a reservoir, fluid permeable support, or fluid permeable membrane of the fluid collection device.

In some examples, the portable vacuum source (e.g., suction device) may be disposed on or within the fluid collection device and applying suction with the portable vacuum source may include activating the portable vacuum source. In some examples, the portable vacuum source may be spaced from the fluid collection device and applying suction with the portable vacuum source may include activating the portable vacuum source.

In some examples, applying suction with a portable vacuum source effective to suction the fluid(s) from the chamber via a conduit disposed therein and in fluid communication with the portable vacuum source may include detecting moisture in the chamber (e.g., via one or more moisture sensors) and responsive thereto, activating the portable vacuum source to provide suction in the chamber. The control of the portable vacuum source responsive to the signals indicating that moisture or a level thereof is present in the chamber can be automatic, such as via a controller (e.g., computer programmed to perform the operation), or may merely provide an indication that a level of moisture is present that may necessitate removal of fluid from the chamber of the fluid collection device. In the latter case, a user may receive the indication (e.g., from the controller) and activate the portable vacuum pump manually.

In an example, the method 800 can include collecting the fluid(s) that are removed from the fluid collection device, such as into a fluid storage container that is spaced from the fluid collection device and in fluid communication with the conduit. The fluid storage container can include any of the fluid storage containers disclosed herein.

While various aspects and embodiments have been disclosed herein, other aspects and embodiments are contemplated. The various aspects and embodiment disclosed herein are for purposes of illustration and are not intended to be limiting.

I claim:

1. A urine collection system, comprising:
a fluid storage container configured to hold a fluid;
a wearable urine collection device in fluid communication with the fluid storage container, the urine collection device including:
a fluid impermeable barrier at least partially defining a chamber, the fluid impermeable barrier also defining an opening extending therethrough, the opening configured to be positioned adjacent to a female urethra or have a male urethra positioned therethrough; and
a conduit including an inlet and an outlet, the inlet being positioned within the urine collection device and the outlet is configured to be in fluid communication with the fluid storage container; and
a portable vacuum source in fluid communication with the fluid storage container, wherein the portable vacuum source is disposed within the fluid impermeable barrier of the urine collection device and the portable vacuum source is configured to draw liquid from the urine collection device;
wherein the conduit includes a first portion extending and connected to the portable vacuum source from outside of the fluid impermeable barrier and a second portion extending from and connected to the portable vacuum source within the fluid impermeable barrier with the inlet positioned in the chamber.

2. The urine collection system of claim 1, wherein the fluid impermeable barrier defines a generally cylindrical shape and the opening is a longitudinally extending opening in the generally cylindrical shape.

3. The urine collection system of claim 2, further comprising:
a fluid permeable membrane disposed within the chamber and extending across the opening; and
a fluid permeable support disposed within the chamber and positioned to support the fluid permeable membrane.

4. The urine collection system of claim 3, wherein:
the fluid impermeable barrier and one or more of the fluid permeable membrane or fluid permeable support define a reservoir therebetween; and
the inlet is disposed in the reservoir.

5. The urine collection system of claim 1, wherein the fluid impermeable barrier has a cupped shape.

6. The urine collection system of claim 1, wherein:
the fluid impermeable barrier has a cupped shape, the chamber is defined within the fluid impermeable barrier, and the urine collection device includes an annular base attached to the fluid impermeable barrier and defining the opening; and
the annular base is sized and shaped to be positioned around a penis so that the penis is positioned within the chamber.

7. The urine collection system of claim 6, wherein the inlet is positioned adjacent to the annular base.

8. The urine collection system of claim 1, wherein the portable vacuum source is located on the fluid impermeable barrier.

9. The urine collection system of claim 1, wherein:

the urine collection device is spaced from and positioned upstream from the fluid storage container; and the portable vacuum source is positioned downstream from the urine collection device.

10. A method to collect urine, the method comprising:

positioning an opening of a wearable urine collection device adjacent to a female urethra or around a male urethra, the opening defined by a fluid impermeable barrier of the urine collection device;

receiving urine from the female urethra or the male urethra into a chamber of the urine collection device, the chamber of the urine collection device at least partially defined by the fluid impermeable barrier; and applying suction with a portable vacuum source disposed within the fluid impermeable barrier of the urine collection device effective to suction liquid from the chamber via a conduit disposed therein and in fluid communication with the portable vacuum source, wherein the conduit includes a first portion extending and connected to the portable vacuum source from outside of the fluid impermeable barrier and a second portion extending from and connected to the portable vacuum source within the fluid impermeable barrier with an inlet positioned in the chamber.

11. The method of claim 10, wherein the portable vacuum source is disposed within the urine collection device and applying suction with the portable vacuum source includes activating the portable vacuum source.

12. The method of claim 10, wherein:

the fluid impermeable barrier also defines the opening configured to be positioned adjacent to a female urethra or have a male urethra positioned therethrough; and the conduit includes the inlet and an outlet, the inlet being positioned within the urine collection device and the outlet is configured to be in fluid communication with a fluid storage container.

13. The method of claim 10, wherein positioning the opening of the urine collection device adjacent to the female urethra or around the male urethra includes positioning the opening over the female urethra.

14. The method of claim 10, wherein positioning the opening of the urine collection device adjacent to the female urethra or around the male urethra includes positioning a penis in the chamber.

15. The method of claim 10, wherein the urine collection device includes:

a fluid permeable membrane disposed within the fluid impermeable barrier; and a fluid permeable support positioned and configured to support the fluid permeable membrane.

16. The method of claim 15, wherein receiving urine from the female urethra or the male urethra into the chamber of the urine collection device includes wicking the urine into the chamber via the fluid permeable membrane and fluid permeable support.

17. A urine collection system, comprising:

a fluid storage container configured to hold a fluid;

a wearable urine collection device in fluid communication with the fluid storage container, the urine collection device including:

a fluid impermeable barrier at least partially defining a chamber, the fluid impermeable barrier also defining an opening configured to be positioned adjacent to a female urethra or have a male urethra positioned therethrough; and a conduit including an inlet and an outlet, the outlet being in fluid communication with the fluid storage container and the inlet being positioned in a portion of the chamber selected to be at a gravimetrically low point of the urine collection device when worn by a user; and a portable vacuum source in fluid communication with the fluid storage container via the conduit, wherein the portable vacuum source is disposed within the fluid impermeable barrier of the fluid collection device and is configured to draw liquid from the urine collection device via the conduit;

wherein the conduit includes a first portion extending and connected to the portable vacuum source from outside of the fluid impermeable barrier and a second portion extending from and connected to the portable vacuum source within the fluid impermeable barrier with the inlet positioned in the chamber.

18. The urine collection system of claim 17, wherein the fluid impermeable barrier defines a generally cylindrical shape with a longitudinally extending opening therein.

19. The urine collection system of claim 17, wherein the fluid impermeable barrier has a cupped shape.

* * * * *